US011279950B2

(12) United States Patent
Yazicioglu et al.

(10) Patent No.: US 11,279,950 B2
(45) Date of Patent: *Mar. 22, 2022

(54) COMPOSITION AND METHODS FOR HIGHLY EFFICIENT GENE TRANSFER USING AAV CAPSID VARIANTS

(71) Applicant: The Children's Hospital of Philadelphia, Philadelphia, PA (US)

(72) Inventors: Mustafa N. Yazicioglu, Broomall, PA (US); Federico Mingozzi, Philadelphia, PA (US); Xavier Anguela, Philadelphia, PA (US); Katherine A. High, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 814 days.

This patent is subject to a terminal disclaimer.

(21) Appl. No.: 15/887,641

(22) Filed: Feb. 2, 2018

(65) Prior Publication Data

US 2018/0245098 A1    Aug. 30, 2018

Related U.S. Application Data

(62) Division of application No. 14/394,454, filed as application No. PCT/US2013/037170 on Apr. 18, 2013, now Pat. No. 9,909,142.

(60) Provisional application No. 61/794,995, filed on Mar. 15, 2013, provisional application No. 61/635,273, filed on Apr. 18, 2012.

(51) Int. Cl.
*C12N 15/86* (2006.01)
*C07K 14/005* (2006.01)
*A61K 48/00* (2006.01)

(52) U.S. Cl.
CPC .............. *C12N 15/86* (2013.01); *A61K 48/00* (2013.01); *C07K 14/005* (2013.01); *C12N 2750/14122* (2013.01); *C12N 2750/14143* (2013.01)

(58) Field of Classification Search
CPC ................................ C12N 15/86; A61K 48/00
See application file for complete search history.

(56) References Cited

U.S. PATENT DOCUMENTS

| 6,127,525 | A  | 10/2000 | Crystal et al. |
| 7,629,322 | B2 | 12/2009 | Kleinschmidt et al. |
| 8,318,687 | B2 | 11/2012 | Tabira et al. |
| 9,909,142 | B2 | 3/2018  | Yazicioglu et al. |
| 2007/0036757 | A1 | 2/2007 | Kleinschmidt et al. |
| 2009/0197338 | A1 | 8/2009 | Vandenberghe et al. |
| 2009/0275107 | A1 | 11/2009 | Lock et al. |

FOREIGN PATENT DOCUMENTS

| JP | 2008-538286 A | 10/2008 |
| RU | 2335542 C2 | 11/2004 |
| WO | 2004/111248 A2 | 12/2004 |
| WO | 2006/110689 A2 | 10/2006 |
| WO | 2011/126808 A9 | 10/2011 |
| WO | 2013/078316 A1 | 5/2013 |

OTHER PUBLICATIONS

Sen et al.; Targeted Modifications in Adeno-Associated Virus Serotype 8 Capsid Improves Its Hepatic Gene Transfer Efficiency In Vivo; Human Gene Therapy Methods, vol. 24, pp. 104-116; Apr. 2013 (Year: 2013).*
Ciechanover, A., The Ubiquitin-Proteasome System: Death of Proteins is Required for Life of Cells, Celltransmissions, 2003, 19(3):3-10.
Duan, et al.: "Endosomal processing limits gene transfer to polarized airway epithelia by adeno-associated virus", Journal of Clinical Investigation American Society for Clinical Investigation, US, vol. 185, No. 11, Jun. 1, 2000, pp. 1573-1587, XP002962239.
Martin, P.T., et al., Overexpression of Galgt2 in Skeletal Muscle Prevents Injury Resulting from Eccentric Contractions in Both MDX and Wild-Type Mice, Am., J. Physiol. Cell Physiol., 2009, 296:C476-C488.
Opie, et al., Identification of Amino Acid Residues in the Capsid Proteins of Adeno-Associated Virus Type 2 That Contribute to Heparan Sulfate Proteoglycan Binding, Journal of Virology, 2003, 77(12):6995-7006.
Sanlioglu, S., et al., Rate Limiting Steps of AAV Transduction and Implications for Human Gene Therapy, Current Gene Therapy, 2001, 1(2):137-147.
Zhong, et al: "Next generation of adena-associated virus 2 vectors: point mutations in tyrosines lead to high-efficiency transduction at lower doses", Proceedings of the National Academy of Sciences, National Academy of Sciences, vol. 105, No. 22, Jun. 3, 2008, pp. 7827-7832, XP002493284.

* cited by examiner

*Primary Examiner* — Antonio Galisteo Gonzalez
(74) *Attorney, Agent, or Firm* — Pillsbury Winthrop Shaw Pittman LLP; Robert M. Bedgood

(57) ABSTRACT

Compositions and methods for AAV mediated gene therapy are disclosed. AAV vectors comprise protein capsid variants comprising therapeutically beneficial transgenes. AAV variants are provided which exhibit increased transduction efficiency when compared to AAV serotypes (e.g., AAV1, AAV2, AAV8, AAV-rh74), which lack the modifications disclosed herein. Such improved vectors are useful for transduction of a variety of tissues.

17 Claims, 20 Drawing Sheets

Specification includes a Sequence Listing.

AAV1

COMPOSITION AND METHODS FOR HIGHLY EFFICIENT GENE TRANSFER USING AAV CAPSID VARIANTS

RELATED APPLICATIONS

This application is a divisional application of U.S. application Ser. No. 14/394,454, filed Oct. 14, 2014, which is the National Phase of International Application No. PCT/US2013/037170, filed Apr. 18, 2013, which designated the U.S. and that International Application was published under PCT Article 21(2) in English, which claims priority to U.S. Provisional Application No. 61/794,995, filed Mar. 15, 2013 and U.S. Provisional Application No. 61/635,273, filed Apr. 18, 2012, all of which applications are expressly incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 2, 2018, is named CHOP_0455963_SEQLIST.TXT and is 34,657 bytes in size.

FIELD OF THE INVENTION

This application relates to the fields of gene therapy and molecular biology. More specifically, this invention provides adeno-associated viral vectors comprising protein capsid variants which improve the transduction efficiency of AAV vectors comprising therapeutically beneficial transgenes.

BACKGROUND OF THE INVENTION

Several publications and patent documents are cited throughout the specification in order to describe the state of the art to which this invention pertains. Each of these citations is incorporated herein by reference as though set forth in full.

Adeno-associated virus (AAV) is a small (20 nm), replication-defective, non-enveloped virus. Many distinct AAV serotypes have been characterized in human and nonhuman primates. The AAV genome is comprised of single-stranded DNA with 145 bp inverted terminal repeats (ITRs) at both ends. There are two open reading frames (ORFs), rep and cap. While the rep products are essential for AAV replication, 3 capsid proteins (VP1, VP2, and VP3) are expressed from the cap gene. VP1, VP2 and VP3 come together at 1:1:10 ratio to form an icosahedral capsid (Xie Q et al, 2002). During recombinant AAV (rAAV) vector production, an expression cassette flanked by ITRs is packaged into AAV capsid. The genes required for replication of AAV are not included in the cassette. Recombinant AAV is considered the safest and one of the most widely used viral vectors for in vivo gene transfer. The vectors can infect cells from multiple tissue types providing strong and persistent transgene expression. They are also non-pathogenic and have a low immunogenicity profile (High KA, 2011).

One of the immediate goals for gene therapy trials is optimizing vectors to maximize tissue transduction while minimizing the vector dose. Upon entry into the cell, AAV capsid proteins are subject to proteasome mediated degradation. Phosphorylation of surface-exposed tyrosine residues of AAV capsid represents one of the first steps that leads to degradation of the virus via the ubiquitin-proteasome pathway (Thong L et al, 2007). Most of the regulated proteolysis in the cell occurs through this pathway. Ubiquitin is a small protein (~8.5 kDa) that can be found in all eukaryotic cells. Ubiquitin is attached to the side-chain of amino-acids of a substrate protein. After additional ubiquitin proteins are attached to the substrate via the initially attached ubiquitin, a polyubiquitin chain is formed and the substrate is marked for degradation (Thrower J S et al 2000, Peng J et al 2003, Bedford L et al 2011). It has been shown that mutation of surface-exposed tyrosine residues leads to an increase in transduction efficiency of AAV2 vectors (Zhong L et al, 2008). More recently, several groups have shown that the strategy is effective also with other AAV serotypes in several tissues, including AAV serotype 6 and 8.

Clearly, a need exists in the art for compositions and methods which improve the transduction of AAV carrying clinically important transgenes in patients in need thereof.

SUMMARY OF THE INVENTION

In accordance with the present invention, novel AAV variants are provided which exhibit increased transduction efficiency when compared to AAV serotypes (e.g., AAV1, AAV2, AAV8, AAV-rh74), which lack the modifications disclosed herein. Such improved vectors are useful for transduction of a variety of tissues, including liver, muscle, brain, and retina.

In one embodiment, an adeno-associated virus (AAV) vector comprising an altered VP1 capsid protein is provided, the altered capsid protein comprising lysine residue substitutions, thereby reducing ubiquination of the capsid and increasing the transduction efficiency of variant AAV into target tissues and cells. In one embodiment, the vector further comprises a heterologous nucleic acid, (e.g., a minigene comprising AAV inverted terminal repeats and a heterologous nucleic acid sequence) operably linked to regulatory sequences which direct expression of a product from the heterologous nucleic acid sequence in a host cell. In a preferred embodiment, the AAV vector comprises one or more lysine substitutions in VP1 as provided in the tables set forth herein. In another embodiment, the AAV vector is of the AAV8 serotype and contains an alteration provided in Table 3.

In a preferred embodiment, the AAV vectors of the invention comprising the variant capsid proteins are useful for expression of therapeutic peptides or therapeutic nucleic acids. Such peptides include, without limitation, an antiviral RNAi molecule, Factor VIII, Factor IX or a functional fragment thereof. Additional expression products include for example, IgG, IgM, IgA, IgD, IgE, chimeric immunoglobulins, humanized antibodies, or single chain antibodies. In one aspect the expression product is an RNAi that is useful for inhibiting HCV infection and replication. In another embodiment, the expression product is an antisense nucleic acid useful for down modulating a target cell of interest.

In another embodiment of the invention, a pharmaceutical composition comprising the variant AAV vectors of the invention in a biologically compatible carrier is provided. Also encompassed by the present invention are cell cultures comprising the vectors disclosed herein.

The invention also encompasses a method of delivering a transgene to a cell in a subject, said method comprising the step of contacting the cell with an AAV vector as disclosed herein, wherein said AAV vector comprises the transgene, wherein the presence of lysine substitution in the VP1 capsid sequence in said vector is associated with reduced ubiquitination and increased transduction efficiency.

In a final aspect, the invention provides decoy viral variants that are inefficient at infecting cells but are effective to block antibody neutralization of viral variants carrying beneficial transgenes due to the structural similarities of the two viral variants. Exemplary capsid variants for this purpose include for example, K38R, K143R, K510R and K709R.

BRIEF DESCRIPTION OF THE DRAWINGS

(FIG. 1A) There are 11 Lysines on the surface of AAV1 VP3. Residue colors are as follows: K258 red, K459 blue, K491 yellow, K493 magenta, K508 cyan, K528 dark salmon, K533 light green, K545 light blue (slate), K567 dark salmon, K666 light cyan, K707 gray. (FIG. 1B) There are 10 Lysines on the surface of AAV2 VP3. Residue colors are as follows: K258 red, K490 yellow, K507 cyan, K527 dark salmon, K532 light green, K544 light blue (slate), K549 light yellow, K556 light magenta, K665 light cyan, K706 gray (FIG. 1C) There are 8 Lysines on the surface of AAV8 VP3. Residue colors are as follows: K259 red, K333 green, K510 cyan, K530 dark salmon, K547 light blue (slate), K569 dark salmon, K668 light cyan, K709 gray. Note that K528 and K567 of AAV1 and K530 and K569 of AAV8 are side by side in the structure and showed with the same color.

(FIG. 2B) K569R and K668R capsid mutations (FIG. 2C) Affect of K38R, K143R, K259R, K510R, K547R capsid mutations are compared to affect of K530R mutation.

(FIG. 3B) K709R mutation negatively affects the AAV8 transduction, Addition of K709R mutation to K(137/333/530)R mutant also decreases the transduction of the virus. (FIG. 3C) Combination of multiple Lysine to arginine mutations does not increase the transduction rate. (FIG. 3D) Combination of three lysine to arginine residues with four or six tyrosine to phenylalanine residues decreases the transduction rate.

(FIG. 4B) Total number of GFP positive cells and GFP expression was compared among different constructs at 50K and 500K MOIs.

(FIG. 5A) AAV2 K137R, K527R or K532R mutants were compared to WT AAV2 in terms of HHL5 cell line transduction rate. The cells were transfected at 10K, 50K, 100K and 500K MOIs and checked 24 hours later for GFP expression. (FIG. 5B) A graph showing cytotoxicity as measured by LDL release of variants tested.

(FIG. 7A) Definition of TMR=K(137/333/530) R, Definition of HMF=Y(253/275/447/703/707/733)F. (FIG. 7B) Definition of HMR: K(137/259/333/530/552/569) R, Definition of 195/202: G195A+L199V+S201P+G202N. While HMR+195/202, HMR+195/202+K(38)R, HMR+195/202+K(51)R, HMR+195/202+K(61)R, and HMR+195/202+K(77)R produced higher hFIX production upon injection to mice, HMR+195/202+K(122/123)R or HMR+195/202+K(142/413)R injection did not produce any detectable hFIX at all. (FIG. 7C): RHM13_1 mutant produced similar hFIX levels compared to Rh74 WT whereas hFIX levels derived from RHM17_1-treated mice were barely above background levels. (FIG. 7D) RHM14_2 mutant produced similar hFIX levels compared to Rh74 WT; RHM15_1 performance was in-between that of AAV8 and AAVrh74 WT.

DETAILED DESCRIPTION OF THE INVENTION

Figure 1A:
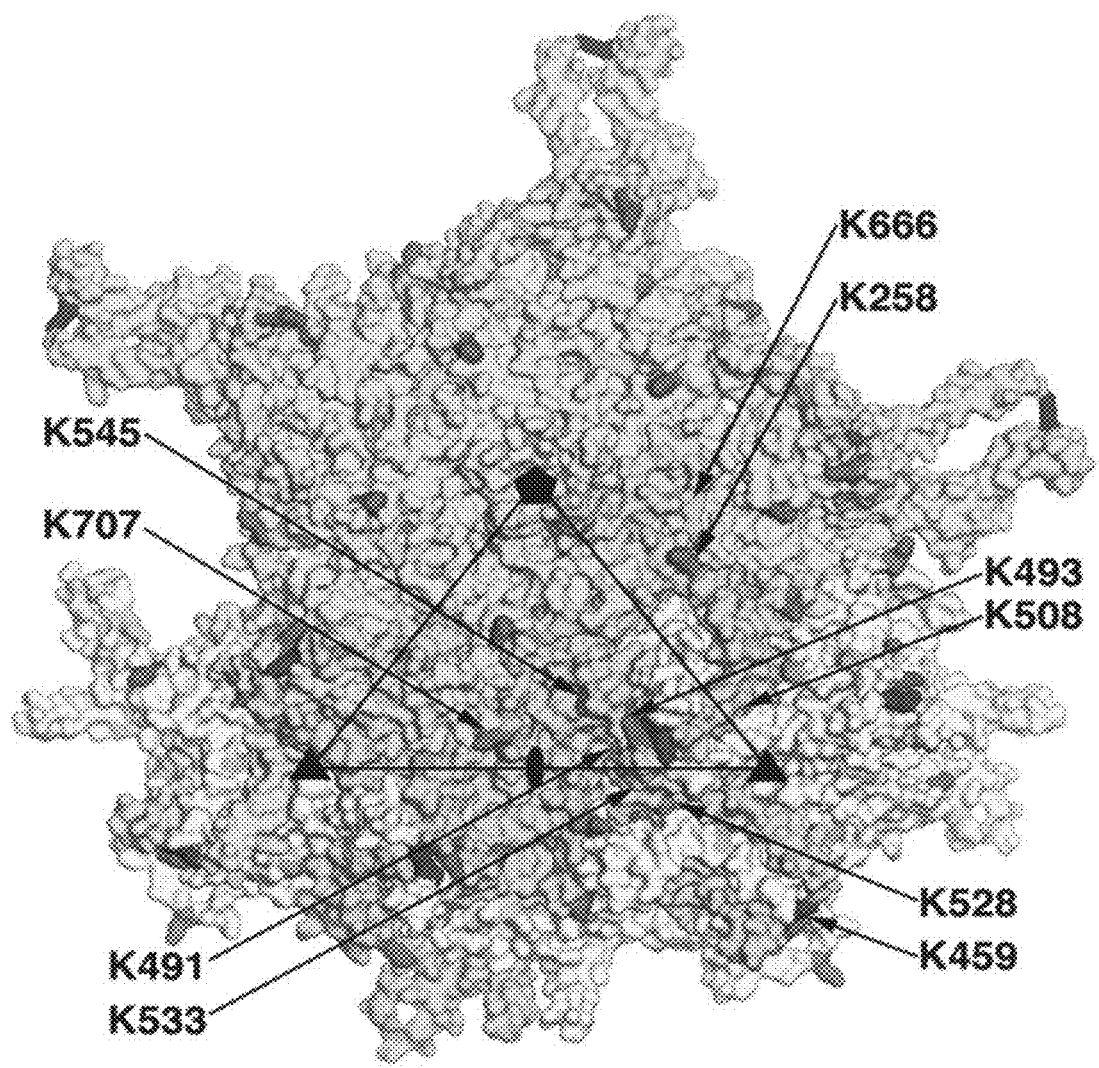
FIGS. 1A-1C: Lysines on the surface of AAV1, AAV2 and AAV8: PDB numbers of AAV serotypes used here are as follows: AAV1: 3NG9, AAV2: 1LP3, and AAV8: 2QA0. The arrows represent the respective Lysine residues.

In accordance with the present invention, we have found that mutating the lysine residues on AAV capsids to arginine residues increases AAV transduction efficiency. Our initial experiments showed that a single substitution of a lysine residue predicted to be a target for ubiquitination resulted in higher levels of expression of the human factor IX (FIX) transgene in mice compared to animals receiving unmodified AAV vectors. The AAV lysine mutants described herein could be used to advantage to generate vectors that target the liver, CNS, muscle, and other organs with higher efficiency compared to the wild type AAV capsids. Thus, this discovery can be used to develop therapeutics to treat hemophilia A, B, Huntington's disease, and virtually any other disease that requires increased transduction levels of desirable transgenes into a target tissue of interest.

The following definitions are provided to facilitate an understanding of the present invention.

I. Definitions

"Gene therapy" is the insertion of genes into an individual's cells and/or tissues to treat a disease, commonly hereditary diseases wherein a defective mutant allele is replaced or supplemented with a functional one.

"Adeno-associated viruses", from the parvovirus family, are small viruses with a genome of single stranded DNA. These viruses can insert genetic material at a specific site on chromosome 19 and are preferred because they are not associated with pathogenic disease in humans.

A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-cancer effects. Therapeutic peptides and proteins include, but are not limited to, CFTR (cystic fibrosis transmembrane regulator protein), dystrophin (including the protein product of dystrophin mini-genes, see, e.g, Vincent et al., (1993) Nature Genetics 5:130), utrophin (Tinsley et al., (1996) Nature 384:349), clotting factors (Factor XIII, Factor IX, Factor X, etc.), monoclonal antibodies (Lewis et al., 2002), erythropoietin, the LDL receptor, lipoprotein lipase, ornithine tranthranscarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, hormones, growth factors (e.g., insulin-like growth factors 1 and 2, platelet derived growth factor, epidermal growth factor, nerve growth factor, neurotrophic factor −3 and −4, brain-derived neurotrophic factor, glial derived growth factor, transforming growth factor α and β, and the like), cytokines (e.g., α-interferon, β-interferon, interferon-γ, interleukin-2, interleukin-4, interleukin 12, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other peptide or protein that has a therapeutic effect in a subject in need thereof.

Further exemplary therapeutic peptides or proteins include those that may be used in the treatment of a disease condition including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system (WO 98/10088); the tetracycline-repressible system (Gossen et al, Proc. Natl. Acad. Sci. USA, 89:5547-5551 (1992)); the tetracycline-inducible system (Gossen et al., Science, 268:1766-1769 (1995); see also Harvey et al., Curr. Opin. Chem. Biol., 2:512-518 (1998)); the RU486-inducible system (Wang et al., Nat. Biotech., 15:239-243 (1997) and Wang et al., Gene Ther., 4:432-441 (1997)]; and the rapamycin-inducible system (Magari et al., J. Clin. Invest., 100:2865-2872 (1997); Rivera et al., Nat. Medicine. 2:1028-1032 (1996)). Other types of inducible promoters which may be useful in this context are those which are regulated by a specific physiological state, e.g., temperature, acute phase, or in replicating cells only.

In another embodiment, the native promoter for the transgene or nucleic acid sequence of interest will be used. The native promoter may be preferred when it is desired that expression of the transgene or the nucleic acid sequence should mimic the native expression. The native promoter may be used when expression of the transgene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In one embodiment, the recombinant viral genome comprises a transgene operably linked to a tissue-specific promoter. For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li et al., Nat. Biotech., 17:241-245 (1999). Examples of promoters that are tissue-specific are known for liver albumin, Miyatake et al. J. Virol., 71:5124-32 (1997); hepatitis B virus core promoter, Sandig et al., Gene Ther. 3:1002-9 (1996); alpha-fetoprotein (AFP), Arbuthnot et al., Hum. Gene Ther., 7:1503-14 (1996)], bone (osteocalcin, Stein et al., Mol. Biol. Rep., 24:185-96 (1997); bone sialoprotein, Chen et al., J. Bone Miner. Res. 11:654-64 (1996)), lymphocytes (CD2, Hansal et al., J. Immunol., 161:1063-8 (1998); immunoglobulin heavy chain; T cell receptor a chain), neuronal (neuron-specific enolase (NSE) promoter, Andersen et al. Cell. Mol. Neurobiol., 13:503-15 (1993); neurofilament light-chain gene, Piccioli et al., Proc. Natl. Acad. Sci. USA, 88:5611-5 (1991); the neuron-specific vgf gene, Piccioli et al., Neuron, 15:373-84 (1995)]; among others.

The term "enhancers" or "enhancer" as used herein can refer to a DNA sequence that is located adjacent to the DNA sequence that encodes a recombinant product. Enhancer elements are typically located upstream of a promoter element or can be located downstream of or within a DNA coding sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, infection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on to or inherited by progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

II. Methods of Using and Methods of Administration of the Variant Adenoassociated Viral Vectors of the Invention The methods of the present invention provide a means for delivering heterologous nucleic acid sequences into a broad range of host cells, including both dividing and non-dividing cells. The vectors and other reagents, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

In addition, the present invention may be employed to deliver nucleic acids encoding monoclonal antibodies or fragments thereof that are known to provide beneficial biological effects to treat or ameliorate the symptoms associated with cancers, infectious diseases, and autoimmune diseases such as rheumatoid arthritis. Other sequences may encode for example cytokines such as interferon-alpha that may modulate the course of a disease.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

Finally, the instant invention finds further use in diagnostic and screening methods, whereby a gene of interest is transiently or stably expressed in a cell culture system, or alternatively, a transgenic animal model.

III. Subjects, Pharmaceutical Formulations, Vaccines, and Modes of Administration The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

In particular embodiments, the present invention provides a pharmaceutical composition comprising a virus particle of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell in which an AAV provirus is integrated into the genome in a pharmaceutically-acceptable carrier or other medicinal agents, pharmaceutical agents, carriers, adjuvants, diluents, etc.

By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering a viral particle or cell directly to a subject.

The present invention further provides a method of delivering a nucleic acid to a cell. For in vitro methods, the virus-may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of a parvovirus vector of the present invention can be accomplished by any other means known in the art.

Recombinant virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell.

The cell to be administered the inventive virus vector may be of any type, including but not limited to neural cells (including cells of the peripheral and central nervous systems, in particular, brain cells), lung cells, retinal cells, epithelial cells (e.g., gut and respiratory epithelial cells), muscle cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). Moreover, the cells can be from any species of origin, as indicated above.

In particular embodiments of the invention, cells are removed from a subject, the parvovirus vector is introduced therein, and the cells are then replaced back into the subject. Methods of removing cells from subject for treatment ex vivo, followed by introduction back into the subject are known in the art. Alternatively, the rAAV vector is introduced into cells from another subject, into cultured cells, or into cells from any other suitable source, and the cells are administered to a subject in need thereof.

Suitable cells for ex vivo gene therapy include, but are not limited to, liver cells, neural cells (including cells of the central and peripheral nervous systems, in particular, brain cells), pancreas cells, spleen cells, fibroblasts (e.g., skin fibroblasts), keratinocytes, endothelial cells, epithelial cells, myoblasts, hematopoietic cells, bone marrow stromal cells, progenitor cells, and stem cells.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "therapeutically-effective amount".

A "therapeutically-effective" amount as used herein is an amount that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of treating subjects in vivo with the inventive virus particles. Administration of the parvovirus particles of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspenions in liquid prior to injection, or as emulsions. Alternatively, one may administer the virus in a local rather than systemic manner, for example in a depot or sustained-release formulation.

In particularly preformed embodiments of the invention, the nucleotide sequence of interest is delivered to the liver of the subject. Administration to the liver may be achieved by any method known in art, including, but not limited to intravenous administration, intraportal administration, intrabilary administration, intra-arterial administration, and direct injection into the liver parenchyma.

Preferably, the cells (e.g., liver cells) are infected by a recombinant parvovirus vector encoding a peptide or protein, the cells express the encoded peptide or protein and secrete it into the circulatory system in a therapeutically-effective amount (as defined above). Alternatively, the vector is delivered to and expressed by another cell or tissue, including but not limited to, brain, pancreas, spleen or muscle.

In other preferred embodiments, the inventive parovirus particles are administered intramuscularly, more preferably by intramuscular injection or by local administration (as defined above). In other preferred embodiments, the parovirus particles of the present invention are administered to the lungs.

The parovirus vector disclosed herein may be administered to the lungs of a subject by any suitable means, but are preferably administered by administering an aerosol suspension of respirable particles comprised of the inventive parovovirus vectors, which the subject inhales. The respirable particles may be liquid or solid. Aerosols of liquid particles comprising the inventive parvovirus vectors may be produced by any suitable means, such as with a pressure-driven aerosol nebulizer or an ultrasonic nebulizer, as is known to those of skill in art. See, e.g. U.S. Pat. No. 4,501,729. Aerosols of solid particles comprising the inventive virus vectors may likewise be produced with any solid particulate medicament aerosol generator, by techniques known in the pharmaceutical art.

Dosages of the inventive parvovirus particles will depend upon the mode of administration, the disease or condition to be treated, the individual subject's condition, the particular virus vector, and the gene to be delivered and can be determined in a routine manner. Exemplary doses for achieving therapeutic effects are virus titers of at least about $10^5$, $10^6$, $10^2$, $10^8$, $10^9$, $10^{10}$, $10^{11}$, $10^{12}$, $10^{13}$, $10^{14}$, $10^{15}$, $10^{16}$ transducting units or more, preferably about $10^8$ to $10^{13}$ transducting units, yet more preferably $10^{12}$ transducing units.

In summary, the parvovirus vectors, reagents, and methods of the present invention can be used to direct a nucleic acid to either dividing or non-dividing cells, and to stably express the heterologous nucleic acid therein. Using this vector system, it is now possible to introduce into cells, in vitro or in vivo, genes that encode proteins that affect cell physiology. The vectors of the present invention can thus be useful in gene therapy for disease states or for experimental modification of cell physiology.

The following example is provided to illustrate certain embodiments of the invention. It is not intended to limit the invention in anyway.

Example I

Lysine to Arginine Mutations Affect AAV Transduction Rate and MHC Delivery Identification of Lysine Residues to be Targeted in AAV1 and AAV8 Vectors We used the UbPred software to predict the possible ubiquitination sites on AAV1, AAV2, AAV8 and Rh74 capsid proteins (Radivojac P et al, 2010). UbPred software is available online at www-ubpred-org-index-html. The output of the analysis is the prediction of the lysine residues important for ubiquitination within the indicated AAV serotype capsid sequence. See FIG. 1 and Table 1. These are the following:

AAV1 Capsid Protein VP1 Sequence: (SEQ ID NO: 1)
MAADGYLPDWLEDNLSEGIREWWDLKPGAPKPKANQQKQDDGRGLVLPGYKYLGPFNGL
DKGEPVNAADAAALEHDKAYDQQLKAGDNPYLRYNHADAEFQERLQEDTSFGGNLGRAVF
QAKKRVLEPLGLVEEGAKTAPGKKRPVEQSPQEPDSSSGIGKTGQQPAKKRLNFGQTGDSES
VPDPQPLGEPPATPAAVGPTTMASGGGAPMADNNEGADGVGNASGNWHCDSTWLGDRVIT
TSTRTWALPTYNNHLYKQISSASTGASNDNHYFGYSTPWGYFDFNRFHCHFSPRDWQRLINN
NWGFRPKRLNFKLFNIQVKEVTTNDGVTTIANNLTSTVQVFSDSEYQLPYVLGSAHQGCLPP
FPADVFMIPQYGYLTLNNGSQAVGRSSFYCLEYFPSQMLRTGNNFTFSYTFEEVPFHSSYAHS
QSLDRLMNPLIDQYLYYLNRTQNQSGSAQNKDLLFSRGSPAGMSVQPKNWLPGPCYRQQRV
SKTKTDNNNSNFTWTGASKYNLNGRESIINPGTAMASHKDDEDKFFPMSGVMIFGKESAGAS
NTALDNVMITDEEEIKATNPVATERFGTVAVNFQSSSTDPATGDVHAMGALPGMVWQDRD
VYLQGPIWAKIPHTDGHFHPSPLMGGFGLKNPPPQILIKNTPVPANPPAEFSATKFASFITQYST
GQVSVEIEWELQKENSKRWNPEVQYTSNYAKSANVDFTVDNNGLYTEPRPIGTRYLTRP

| Lysine position | Score | Ubiquitinated |
|---|---|---|
| 26 | 0.59 | No |
| 31 | 0.55 | No |
| 33 | 0.47 | No |
| 38 | 0.61 | No |
| 51 | 0.54 | No |
| 61 | 0.72 | Yes Medium confidence |
| 77 | 0.63 | Yes Low confidence |
| 84 | 0.72 | Yes Medium confidence |
| 122 | 0.17 | No |
| 123 | 0.26 | No |
| 137 | 0.90 | Yes High confidence |
| 142 | 0.62 | Yes Low confidence |
| 143 | 0.81 | Yes Medium confidence |
| 161 | 0.70 | Yes Medium confidence |
| 168 | 0.25 | No |
| 169 | 0.26 | No |
| 258 | 0.49 | No |
| 310 | 0.14 | No |
| 315 | 0.15 | No |
| 322 | 0.48 | No |
| 459 | 0.81 | Yes Medium confidence |
| 476 | 0.43 | No |
| 491 | 0.20 | No |
| 493 | 0.28 | No |
| 508 | 0.62 | Yes Low confidence |
| 528 | 0.67 | Yes Low confidence |
| 533 | 0.70 | Yes Medium confidence |
| 545 | 0.65 | Yes Low confidence |
| 567 | 0.66 | Yes Low confidence |
| 621 | 0.50 | No |
| 641 | 0.50 | No |
| 650 | 0.45 | No |

-continued

| | | |
|---|---|---|
| 666 | 0.58 | No |
| 689 | 0.65 | Yes Low confidence |
| 693 | 0.65 | Yes Low confidence |
| 707 | 0.78 | Yes Medium confidence |

Legend:

| Label | Score range | Sensitivity | Specificity |
|---|---|---|---|
| Low confidence | 0.62 < s < 0.69 | 0.464 | 0.903 |
| Medium confidence | 0.69 < s < 0.84 | 0.346 | 0.950 |
| High confidence | 0.84 < s < 1.00 | 0.197 | 0.989 |

Desirable mutants in AAV-1

| ID | AAV-1 mutant |
|---|---|
| MUT1-1 | K61R |
| MUT1-2 | K84R |
| MUT1-3 | K137R |
| MUT1-4 | K143R |
| MUT1-5 | K161R |
| MUT1-6 | K459R |
| MUT1-7 | K528R |
| MUT1-8 | K533R |
| MUT1-9 | K707R |

AAV8 capsid protein VP1 sequence: (SEQ ID NO: 2)
MAADGYLPDWLEDNLSEGIREWWALKPGAPKPKANQQKQDDGRGLVLPGYKYLGPFNGL
DKGEPVNAADAAALEHDKAYDQQLQAGDNPYLRYNHADAEFQERLQEDTSFGGNLGRAVF
QAKKRVLEPLGLVEEGAKTAPGKKRPVEPSPQRSPDSSTGIGKKGQQPARKRLNFGQTGDSE
SVPDPQPLGEPPAAPSGVGPNTMAAGGGAPMADNNEGADGVGSSSGNVVHCDSTWLGDRVI
TTSTRTWALPTYNNHLYKQISNGTSGGATNDNTYFGYSTPWGYFDFNRFHCHFSPRDWQRLI
NNNWGFRPKRLSFKLFNIQVKEVTQNEGTKTIANNLTSTIQVFTDSEYQLPYVLGSAHQGCLP
PFPADVFMIPQYGYLTLNNGSQAVGRSSFYCLEYFPSQMLRTGNNFQFTYTFEDVPFHSSYAH
SQSLDRLMNPLIDQYLYYLSRTQTTGGTANTQTLGFSQGGPNTMANQAKNWLPGPCYRQQR
VSTTTGQNNNSNFAWTAGTKYHLNGRNSLANPGIAMATHKDDEERFFPSNGILIFGKQNAAR
DNADYSDVMLTSEEEIKTTNPVATEEYGIVADNLQQQNTAPQIGTVNSQGALPGMVWQNRD
VYLQGPIWAKIPHTDGNFHPSPLMGGFGLKHPPPQILIKNTPVPADPPTTFNQSKLNSFITQYST
GQVSVEIEWELQKENSKRWNPEIQYTSNYYKSTSVDFAVNTEGVYSEPRPIGTRYLTRNL

| Lysine position | Score | Ubiquitinated |
|---|---|---|
| 26 | 0.52 | No |
| 31 | 0.51 | No |
| 33 | 0.16 | No |
| 38 | 0.62 | Yes Low confidence |
| 51 | 0.56 | No |

| | | | -continued |
|---|---|---|---|
| 61 | 0.68 | Yes | Low confidence |
| 77 | 0.65 | Yes | Low confidence |
| 122 | 0.17 | No | |
| 123 | 0.32 | No | |
| 137 | 0.92 | Yes | High confidence |
| 142 | 0.53 | No | |
| 143 | 0.65 | Yes | Low confidence |
| 162 | 0.28 | No | |
| 163 | 0.29 | No | |
| 170 | 0.24 | No | |
| 259 | 0.49 | No | |
| 312 | 0.09 | No | |
| 317 | 0.12 | No | |
| 324 | 0.43 | No | |
| 333 | 0.75 | Yes | Medium confidence |
| 478 | 0.59 | No | |
| 510 | 0.50 | No | |
| 530 | 0.71 | Yes | Medium confidence |
| 547 | 0.40 | No | |
| 569 | 0.66 | Yes | Low confidence |
| 623 | 0.47 | No | |
| 643 | 0.44 | No | |
| 652 | 0.51 | No | |
| 668 | 0.64 | Yes | Low confidence |
| 691 | 0.66 | Yes | Low confidence |
| 695 | 0.67 | Yes | Low confidence |
| 709 | 0.68 | Yes | Low confidence |

| Legend: | | | |
|---|---|---|---|
| Label | Score range | Sensitivity | Specificity |
| Low confidence | 0.62 < s < 0.69 | 0.464 | 0.903 |
| Medium confidence | 0.69 < s < 0.84 | 0.346 | 0.950 |
| High confidence | 0.84 < s < 1.00 | 0.197 | 0.989 |

Table 3 appended hereto provides the yield of vector obtained using the different capsid mutants, including AAV8 of the invention. The table also indicates whether the mutation resulted in increased, decreased or comparable transduction efficiencies when compared to wild type vectors of the same serotype.

AAV2 capsid protein VP1 sequence: (SEQ ID NO: 3)
MAADGYLPDWLEDTLSEGIRQWWKLKPGPPPPKPAERHKDDSRGLVLPGYKYLGPFNGLDK
GEPVNEADAAALEHDKAYDRQLDSGDNPYLKYNHADAEFQERLKEDTSFGGNLGRAVFQA
KKRVLEPLGLVEEPVKTAPGKKRPVEHSPVEPDSSSGTGKAGQQPARKRLNFGQTGDADSVP
DPQPLGQPPAAPSGLGTNTMATGSGAPMADNNEGADGVGNSSGNWHCDSTWMGDRVITTS
TRTWALPTYNNHLYKQISSQSGASNDNHYFGYSTPWGYFDFNRFHCHFSPRDWQRLINNNW
GFRPKRLNFKLFNIQVKEVTQNDGTTTIANNLTSTVQVFTDSEYQLPYVLGSAHQGCLPPFPA
DVFMVPQYGYLTLNNGSQAVGRSSFYCLEYFPSQMLRTGNNFTFSYTFEDVPFHSSYAHSQS
LDRLMNPLIDQYLYYLSRTNTPSGTTTQSRLQFSQAGASDIRDQSRNWLPGPCYRQQRVSKT
SADNNNSEYSWTGATKYHLNGRDSLVNPGPAMASHKDDEEKFFPQSGVLIFGKQGSEKTNV
DIEKVMITDEEEIRTTNPVATEQYGSVSTNLQRGNRQAATADVNTQGVLPGMVWQDRDVYL
QGPIWAKIPHTDGHFHPSPLMGGFGLKHPPPQILIKNTPVPANPSTTFSAAKFASFITQYSTGQ
VSVEIEWELQKENSKRWNPEIQYTSNYNKSVNVDFTVDTNGVYSEPRPIGTRYLTRNL

| Lysine position | Score | Ubiquitinated |
|---|---|---|
| 24 | 0.20 | No |
| 26 | 0.49 | No |
| 33 | 0.38 | No |
| 39 | 0.89 | Yes High confidence |
| 51 | 0.53 | No |
| 61 | 0.67 | Yes Low confidence |
| 77 | 0.68 | Yes Low confidence |
| 92 | 0.56 | No |
| 105 | 0.58 | No |
| 122 | 0.14 | No |
| 123 | 0.18 | No |
| 137 | 0.87 | Yes High confidence |
| 142 | 0.58 | No |
| 143 | 0.77 | Yes Medium confidence |
| 161 | 0.70 | Yes Medium confidence |
| 169 | 0.31 | No |
| 258 | 0.51 | No |
| 309 | 0.14 | No |
| 314 | 0.17 | No |
| 321 | 0.46 | No |
| 490 | 0.73 | Yes Medium confidence |
| 507 | 0.61 | No |
| 527 | 0.78 | Yes Medium confidence |
| 532 | 0.75 | Yes Medium confidence |
| 544 | 0.61 | No |
| 549 | 0.68 | Yes Low confidence |
| 556 | 0.62 | Yes Low confidence |
| 620 | 0.47 | No |
| 640 | 0.45 | No |
| 649 | 0.42 | No |
| 665 | 0.54 | No |
| 688 | 0.68 | Yes Low confidence |

-continued

| | | | |
|---|---|---|---|
| 692 | 0.68 | Yes Low confidence | |
| 706 | 0.66 | Yes Low confidence | |

Legend:

| Label | Score range | Sensitivity | Specificity |
|---|---|---|---|
| Low confidence | 0.62 < s < 0.69 | 0.464 | 0.903 |
| Medium confidence | 0.69 < s < 0.84 | 0.346 | 0.950 |
| High confidence | 0.84 < s < 1.00 | 0.197 | 0.989 |

AAV-Rh74 capsid protein VP1 sequence (SEQ ID NO: 4)
MAADGYLPDWLEDNLSEGIREWWDLKPGAPKPKANQQKQDNGRGLVLPGYKYLGPFNGL
DKGEPVNAADAAALEHDKAYDQQLQAGDNPYLRYNHADAEFQERLQEDTSFGGNLGRAVF
QAKKRVLEPLGLVESPVKTAPGKKRPVEPSPQRSPDSSTGIGKKGQQPAKKRLNFGQTGDSES
VPDPQPIGEPPAGPSGLGSGTMAAGGGAPMADNNEGADGVGSSSGNWHCDSTWLGDRVITT
STRTWALPTYNNHLYKQISNGTSGGSTNDNTYFGYSTPWGYFDFNRFHCHFSPRDWQRLINN
NWGFRPKRLNFKLFNIQVKEVTQNEGTKTIANNLTSTIQVFTDSEYQLPYVLGSAHQGCLPPF
PADVFMIPQYGYLTLNNGSQAVGRSSFYCLEYFPSQMLRTGNNFEFSYNFEDVPFHSSYAHS
QSLDRLMNPLIDQYLYYLSRTQSTGGTAGTQQLLFSQAGPNNMSAQAKNWLPGPCYRQQRV
STTLSQNNNSNFAWTGATKYHLNGRDSLVNPGVAMATHKDDEERFFPSSGVLMFGKQGAG
KDNVDYSSVMLTSEEEIKTTNPVATEQYGVVADNLQQQNAAPIVGAVNSQGALPGMVWQN
RDVYLQGPIWAKIPHTDGNFHPSPLMGGFGLKHPPPQILIKNTPVPADPPTFFNQAKLASHTQ
YSTGQVSVEIEWELQKENSKRWNPEIQYTSNYYKSTNVDFAVNTEGTYSEPRPIGTRYLTRNL

| Lysine position | Score | Ubiquitinated |
|---|---|---|
| 26 | 0.60 | No |
| 31 | 0.53 | No |
| 33 | 0.27 | No |
| 38 | 0.23 | No |
| 51 | 0.38 | No |
| 61 | 0.68 | Yes Low confidence |
| 77 | 0.65 | Yes Low confidence |
| 122 | 0.17 | No |
| 123 | 0.30 | No |
| 137 | 0.90 | Yes High confidence |
| 142 | 0.35 | No |
| 143 | 0.35 | No |
| 162 | 0.36 | No |
| 163 | 0.33 | No |
| 169 | 0.27 | No |
| 170 | 0.25 | No |
| 259 | 0.46 | No |
| 312 | 0.13 | No |
| 317 | 0.16 | No |
| 324 | 0.46 | No |
| 333 | 0.77 | Yes Medium confidence |
| 478 | 0.51 | No |
| 510 | 0,49 | No |

| | | | |
|---|---|---|---|
| 530 | 0.67 | Yes | Low confidence |
| 547 | 0.52 | No | |
| 552 | 0.69 | Yes | Medium confidence |
| 569 | 0.67 | Yes | Low confidence |
| 623 | 0.49 | No | |
| 643 | 0.44 | No | |
| 652 | 0.54 | No | |
| 668 | 0.56 | No | |
| 691 | 0.68 | Yes | Low confidence |
| 695 | 0.67 | Yes | Low confidence |
| 709 | 0,69 | Yes | Medium confidence |

Legend:

| Label | Score range | Sensitivity | Specificity |
|---|---|---|---|
| Low confidence | 0.62 < s < 0.69 | 0.464 | 0.903 |
| Medium confidence | 0.69 < s < 0.84 | 0.346 | 0.950 |
| High confidence | 0.84 < s < 1.00 | 0.197 | 0.989 |

Desirable mutants in AAV-rh74 (also see Table 3)

| ID | AAV-rh74 mutant |
|---|---|
| Mut74-1 | K26R |
| Mut74-2 | K31R |
| Mut74-3 | K33R |
| Mut74-4 | K38R |
| Mut74-5 | K51R |
| Mut74-6 | K77R |
| Mut74-7 | K137R |
| Mut74-8 | K163R |
| Mut74-9 | K169R |
| Mut74-10 | K259R |
| Mut74-11 | K333R |
| Mut74-12 | K530R |
| Mut74-13 | K547R |
| Mut74-14 | K552R |
| Mut74-15 | K569R |
| Mut74-16 | K668R |
| Mut74-17 | K691R |
| Mut74-18 | K695R |
| Mut74-19 | K709R |

The following primer sets were utilized to create the lysine containing capsid variants of the invention:

Primers used for Mutagenesis:

```
AAV1 primers:
AAV1 K61R
Sense:
                                            (SEQ ID NO: 5)
5'-CTT CAA CGG ACT CGA CAG GGG GGA GCC-3'

Antisense:
                                            (SEQ ID NO: 6)
5'-GGC TCC CCC CTG TCG AGT CCG TTG AAG-3'

AAV1 K84R
Sense:
                                            (SEQ ID NO: 7)
5'-GCC TAC GAC CAG CAG CTC AGA GCG GGT GAC-3'

Antisense:
                                            (SEQ ID NO: 8)
5'-GTC ACC CGC TCT GAG CTG CTG GTC GTA GGC-3'

AAV1 K137R
Sense:
                                            (SEQ ID NO: 9)
5'-TGG TTG AGG AAG CGC TAG GAC GGC TC CT-3'

Antisense:
                                            (SEQ ID NO: 10)
5'-AGG AGC CGT CCT AGC GCC TTC CTC AAC CA-3'

AAV1 K143R
Sense:
                                            (SEQ ID NO: 11)
5'-CTA AGA CGG CTC CTG AAA GAC GTC CGG TAG-3'

Antisense:
                                            (SEQ ID NO: 12)
5'-CTA CCG GAC GTC TTT CAG GAG CCG TCT TAG-3'

AAV1 K161R
Sense:
                                            (SEQ ID NO: 13)
5'-CGG GCA TCG GCA GGA CAG GCC AGC A-3'

Antisense:
                                            (SEQ ID NO: 14)
5'-TGC TGG CCT GTC CTG CCG ATG CCC G-3'

AAV1 K459R
Sense:
                                            (SEQ ID NO: 15)
5'-AGT CCG GAA GTG CCC AAA ACA GGG ACT GCT GT-3'
```

-continued

Antisense:
(SEQ ID NO: 16)
5'-ACA GCA AGT CCC TGT TTT GGG CAC TTC CGG ACT-3'

AAV1 K528R
Sense:
(SEQ ID NO: 17)
5'-GCA CTG CTA TGG CCT CAC ACA GAG ACG ACG AAG-3'

Antisense:
(SEQ ID NO: 18)
5'-CTT CGT CGT CTC TGT GTG AGG CCA TAG CAG TGC-3'

AAV1 K533R
Sense:
(SEQ ID NO: 19)
5'-CAA AGA CGA CGA AGA CAG GTT CTT TCC CAT GAG CG-3'

Antisense:
(SEQ ID NO: 20)
5'-CGC TCA TGG GAA AGA ACC TGT CTT CGT CGT CTT TG-3'

AAV1 K707R
Sense:
(SEQ ID NO: 21)
5'-TGCAGTACACATCCAATTATGCAAGATCTGCCAACG TTG-3'

Antisense:
(SEQ ID NO: 22)
5'-CAACGTTGGCAGATCTTGCATAATTGGATGTGTACTGCA-3'

AAV8 Primers
AAV8 K137R
Sense:
(SEQ ID NO: 23)
5'-GGT TGA GGA AGG CGC TAG GAC GGC TCC TGG-3'

Antisense:
(SEQ ID NO: 24)
5'-CCA GGA GCC GTC CTA GCG CCT TCC TCA ACC-3'

AAV8 K333R
Sense:
(SEQ ID NO: 25)
5'-GCA GAA TGA AGG CAC CAG GAC CAT CGC CAA TAA CC-3'

Antisense:
(SEQ ID NO: 26)
5'-GGT TAT TGG CGA TGG TCC TGG TGC CTT CAT TCT GC-3'

AAV8 K530R
Sense:
(SEQ ID NO: 27)
5'-GCA TCG CTA TGG CAA CAC ACA GAG ACG ACG AGG-3'

Antisense:
(SEQ ID NO: 28)
5'-CCT CGT CGT CTC TGT GTG TTG CCA TAG CGA TGC-3'

AAV8 K709R
Sense:
(SEQ ID NO: 29)
5'-GTACACCTCCAACTACTACAGATCTACAAGTGTGGACTTTG-3'

Antisense:
(SEQ ID NO: 30)
5'-CAAAGTCCACACTTGTAGATCTGTAGTAGTTGGAGGTGTAC-3'

AAV2 Primers
AAV2 K39R
Sense:
(SEQ ID NO: 31)
5'-GCCCGCAGAGCGGCATAGGGACGACAG-3'

Antisense:
(SEQ ID NO: 32)
5'-CTGTCGTCCCTATGCCGCTCTGCGGGC-3'

AAV2 K137R
Sense:
(SEQ ID NO: 33)
5'-CCTGGTTGAGGAACCTGTTAGGACGGCTCCGG-3'

Antisense:
(SEQ ID NO: 34)
5'-CCGGAGCCGTCCTAACAGGTTCCTCAACCAGG-3'

AAV2 K143R
Sense:
(SEQ ID NO: 35)
5'-AGACGGCTCCGGGAAAAAGGAGGCCGGTA-3'

Antisense:
(SEQ ID NO: 36)
5'-TACCGGCCTCCTTTTTCCCGGAGCCGTCT-3'

AAV2 K161R
Sense:
(SEQ ID NO: 37)
5'-CCTCGGGAACCGGAAGGGCGGGCC-3'

Antisense:
(SEQ ID NO: 38)
5'-GGCCCGCCCTTCCGGTTCCCGAGG-3'

AAV2 K490R
Sense:
(SEQ ID NO: 39)
5'-CCGCCAGCAGCGAGTATCAAGGACATCTGCGG-3'

Antisense:
(SEQ ID NO: 40)
5'-CCGCAGATGTCCTTGATACTCGCTGCTGGCGG-3'

AAV2 K527R
Sense:
(SEQ ID NO: 41)
5'-CGGCCATGGCAAGCCACAGGGACGATGAA-3'

Antisense:
(SEQ ID NO: 42)
5'-TTCATCGTCCCTGTGGCTTGCCATGGCCG-3'

AAV2 K532R
Sense:
(SEQ ID NO: 43)
5'-ACAAGGACGATGAAGAAAGGTTTTTTCCTCAGAGCGG-3'

Antisense:
(SEQ ID NO: 44)
5'-CCGCTCTGAGGAAAAAACCTTTCTTCATCGTCCTTGT-3'

AAV-rh74 Primers
AAV-rh74 K137R
Sense:
(SEQ ID NO: 45)
5'-CTGGTTGAATCGCCGGTTAGGACGGCTCCTG-3

Antisense:
(SEQ ID NO: 46)
5'-GACCAACTTAGCGGCCAATCCTGCCGAGGAC-3'

AAV-rh74 K333R
Sense:
(SEQ ID NO: 47)
5'-GCAGAATGAAGGCACCAGGACCATCGCCAATAACC-3'

Antisense:
(SEQ ID NO: 48)
5'-GGTTATTGGCGATGGTCCTGGTGCCTTCATTCTGC-3'

-continued

AAV-rh74 K530R
Sense:
(SEQ ID NO: 49)
5'-GTTGCCATGGCTACCCACAGGGACGACGAA-3'

Antisense:
(SEQ ID NO: 50)
5'-TTCGTCGTCCCTGTGGGTAGCCATGGCAAC-3'

AAV-rh74 K552R
Sense:
(SEQ ID NO: 51)
5'-GGAAACAGGGAGCTGGAAGAGACAACGTGGACTAT-3'

Antisense:
(SEQ ID NO: 52)
5'-ATAGTCCACGTTGTCTCTTCCAGCTCCCTGTTTCC-3'

AAV-rh74 K569R
Sense:
(SEQ ID NO: 53)
5'-CTAACCAGCGAGGAAGAAATAAGGACCACCAACCC-3'

Antisense:
(SEQ ID NO: 54)
5'-GGGTTGGTGGTCCTTATTTCTTCCTCGCTGGTTAG-3'

AAV-rh74 K691R
Sense:
(SEQ ID NO: 55)
5'-CGAGTGGGAGCTGCAGAGGGAGAACAGCAA-3'

Antisense:
(SEQ ID NO: 56)
5'-TTGCTGTTCTCCCTCTGCAGCTCCCACTCG-3'

AAV-rh74 K695R
Sense:
(SEQ ID NO: 57)
5'-GCTGCAGAAGGAGAACAGCAGACGCTGGAACC-3'

Antisense:
(SEQ ID NO: 58)
5'-GGTTCCAGCGTCTGCTGTTCTCCTTCTGCAGC-3'

AAV-rh74 K709R
Sense:
(SEQ ID NO: 59)
5'-AGTACACTTCCAACTACTACAGATCTACAAATGTGGACTTTGC-3'

Antisense:
(SEQ ID NO: 60)
5'-GCAAAGTCCACATTTGTAGATCTGTAGTAGTTGGAAGTGTACT-3'

Table 5 provides a series of AAV vectors derived from mutagenesis that were used to package liver-specific AAV transgene expression cassettes for FIX. Packaging efficiency was indistinguishable from that observed with wild type, unmodified AAV8 vectors.

| Lot number | Lysine mutant | Preparation size (Roller Bottles) | Yield per roller bottle (vector genomes) |
|---|---|---|---|
| KA712 | AAV8 K137R | 10 | 1.53E13 |
| KA713 | AAV8 K333R | 10 | 9.46E12 |
| KA714 | AAV8 K530R | 10 | 1.61E13 |
| KA535 | AAV8 (wild type) | 10 | 6.63E12 |

Capsid mutants which contain 2, 3, 4, 5, 6, 7 or more altered lysine residues in any of the capsid proteins described herein to further increase transduction efficiency are also within the scope of the invention. The data also reveals that certain mutations result in variants which exhibited significantly reduced transduction efficiency. Such variants could be used in combination with variants which exhibit increased transduction efficiencies, to act as decoys to neutralize or saturate an antibody directed immune response to the incoming vectors, thereby enabling vectors carrying desirable transgenes to more efficiently enter cells.

Figure 1B:
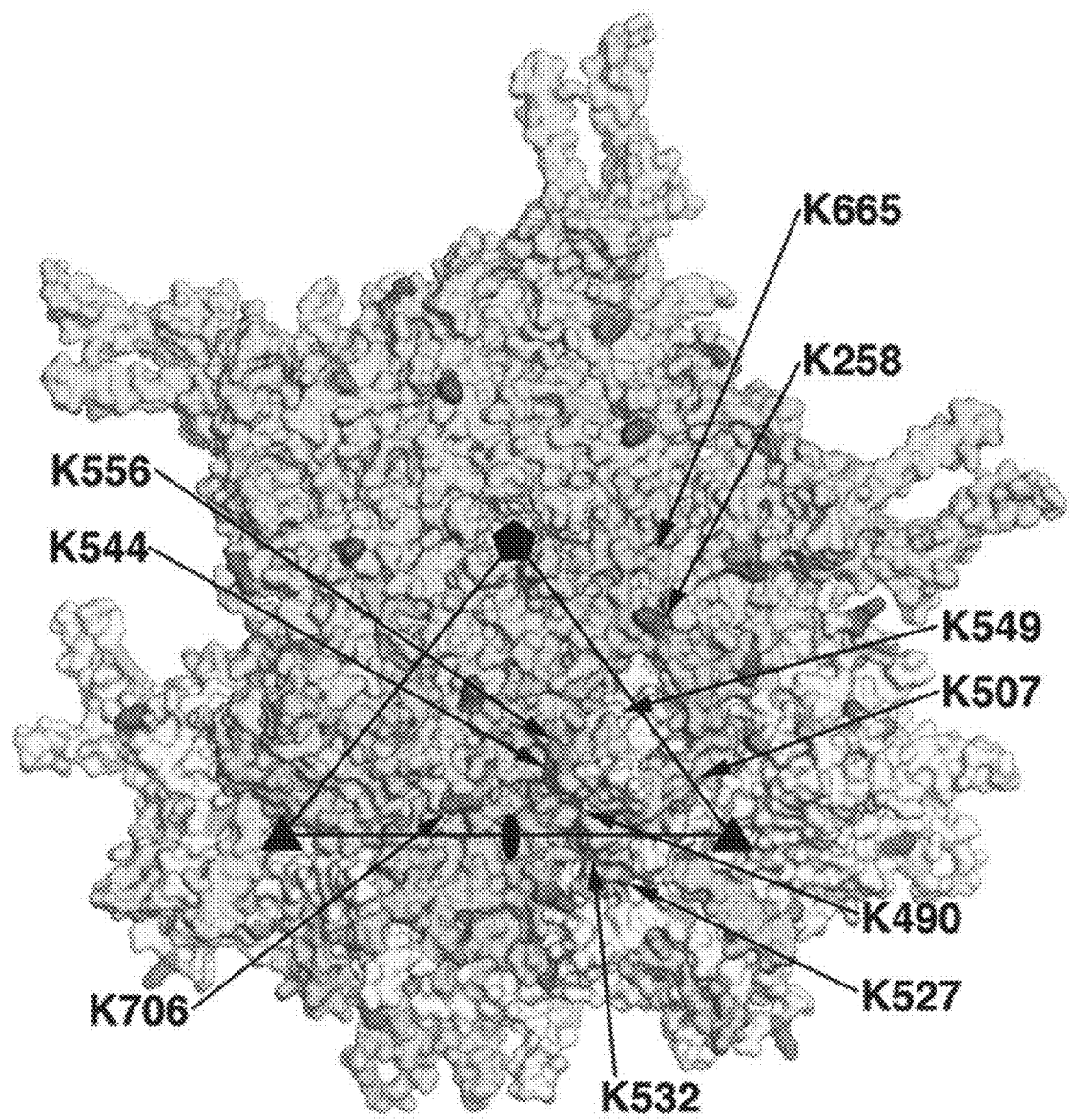
Figure 1C:
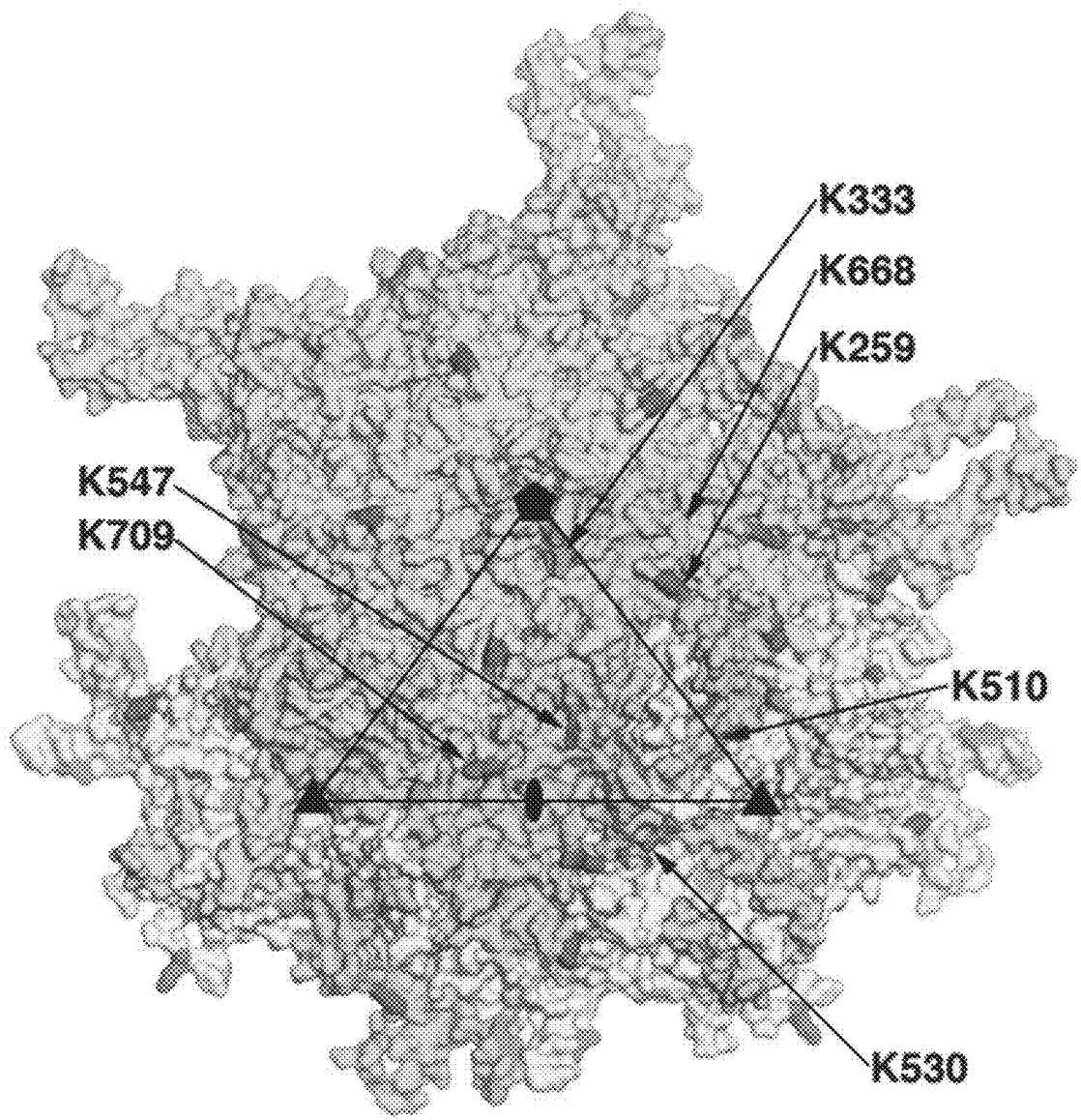
Figure 2A:
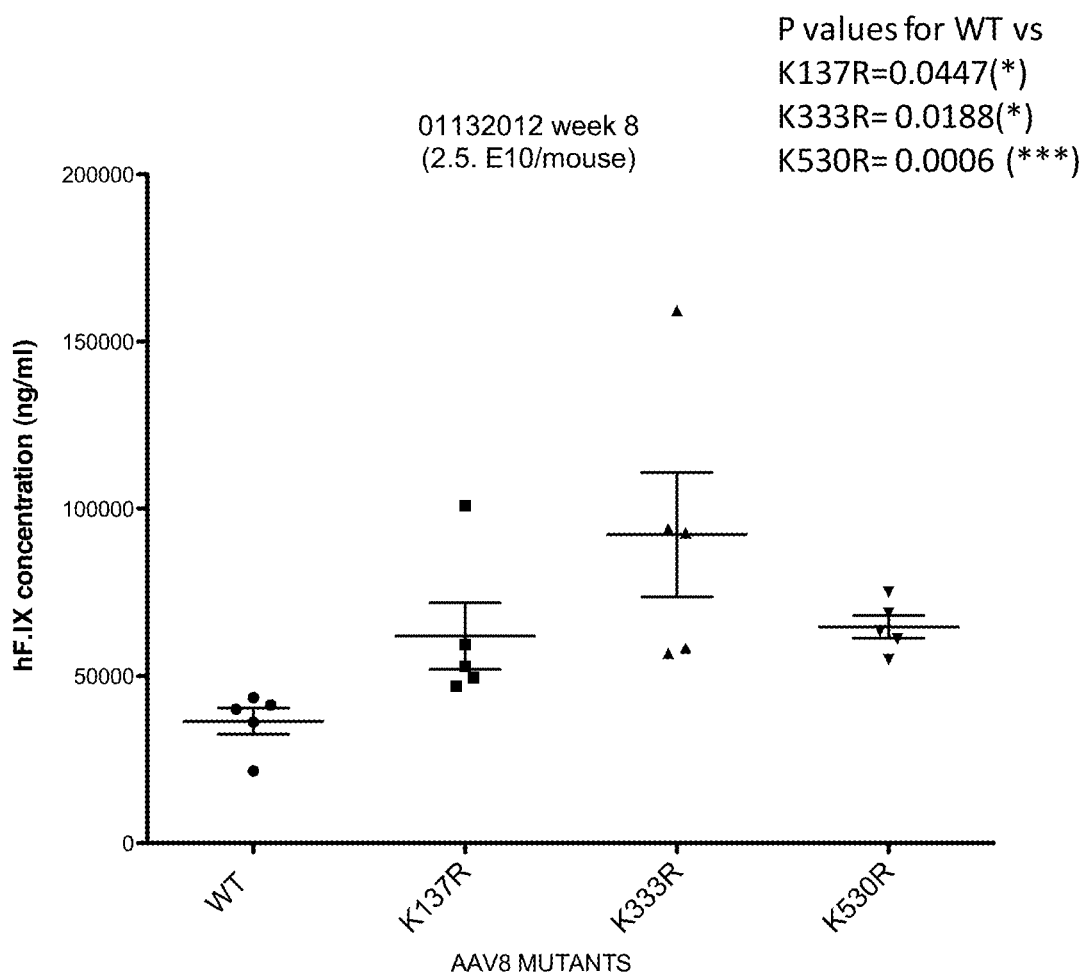
FIGS. 2A-2C: Several Lysine residues of AAV8 capsid were mutated to Arginine. Blood from the animals was collected 8 weeks after virus injection via tail vein. hF.IX levels are detected by ELISA (FIG. 2A) The residues that are predicted to be ubiqutinated by the software with high and medium confidence levels were mutated to arginine. $2.5 \times 10^{10}$ virus particles per mouse were injected via tail vein (FIGS. 2B, 2C) The residues that are predicted with low confidence to be ubiqutinated by the software were mutated to arginine. $2.5 \times 10^9$ virus particles per mouse were injected via tail vein.
Figure 2B:
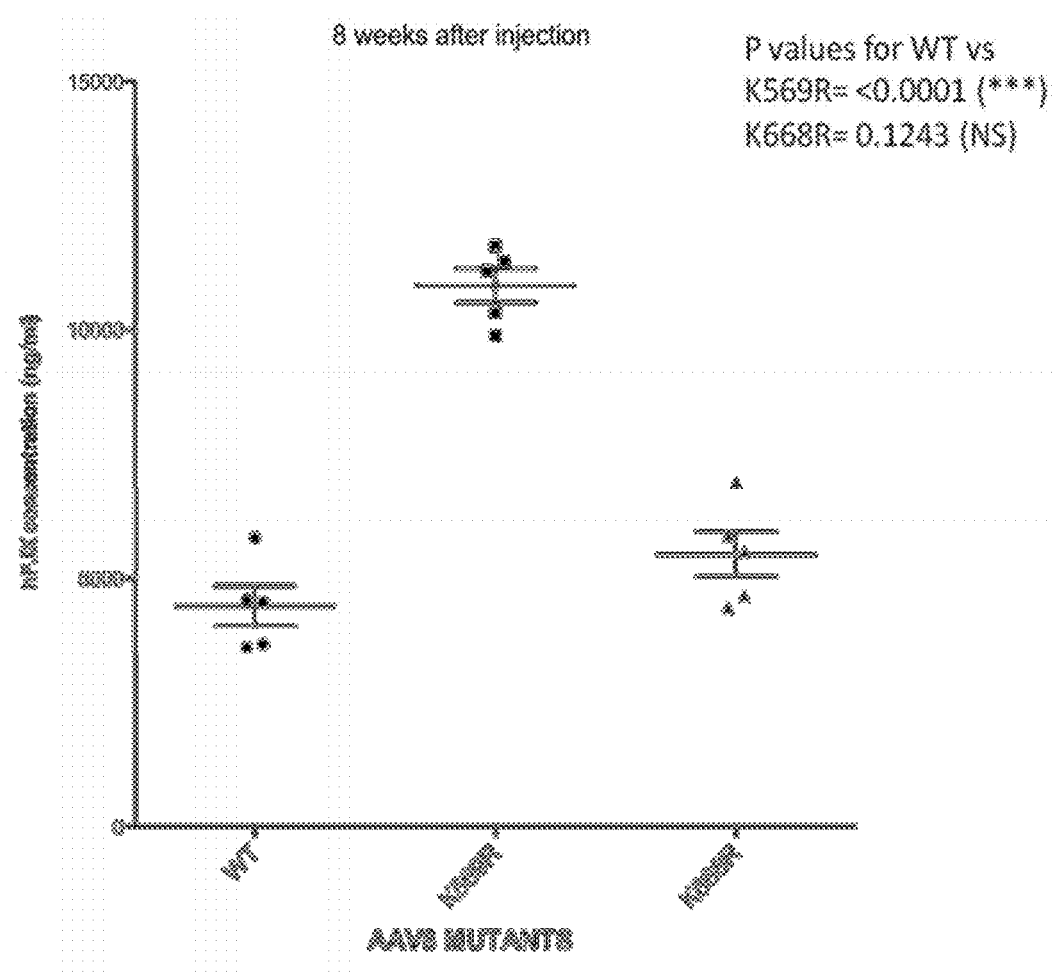
Figure 2C:
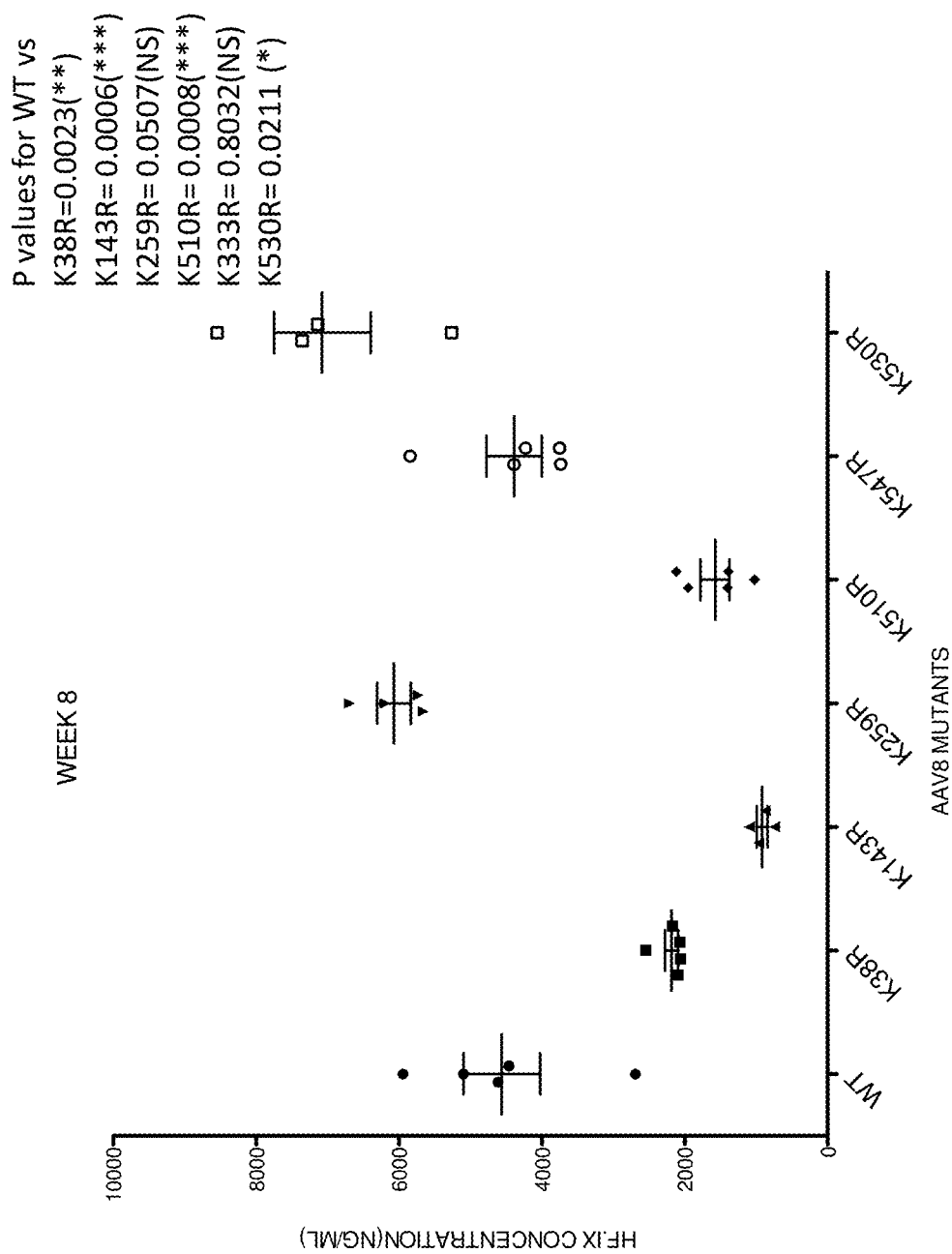
Figure 3A:
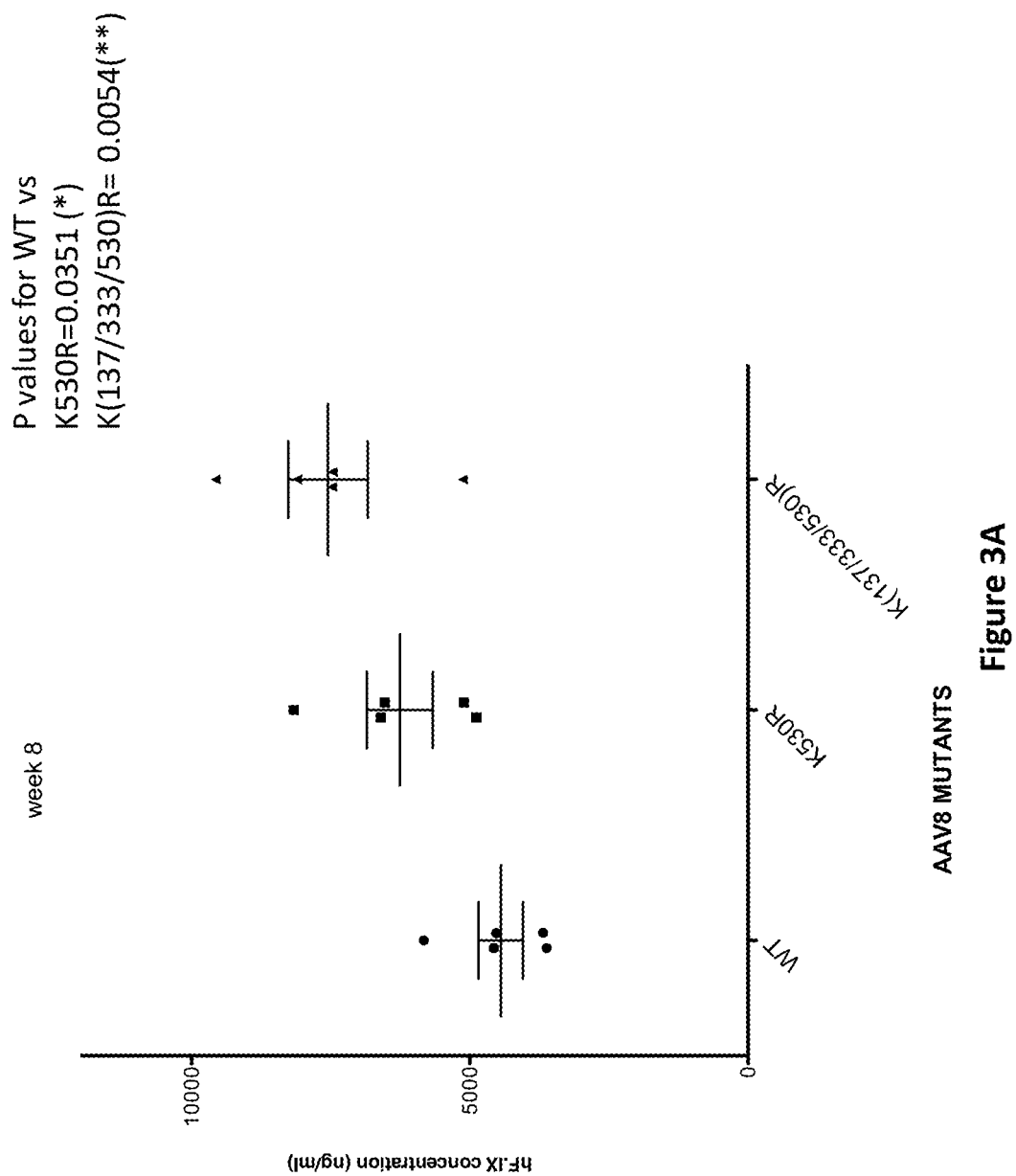
FIGS. 3A-3D: Combination of the K to R capsid mutations (FIG. 3A) Combination of K137R, K33R and K530R mutations are still higher than the wild type but not statistically different from the K530R.
Figure 3B:
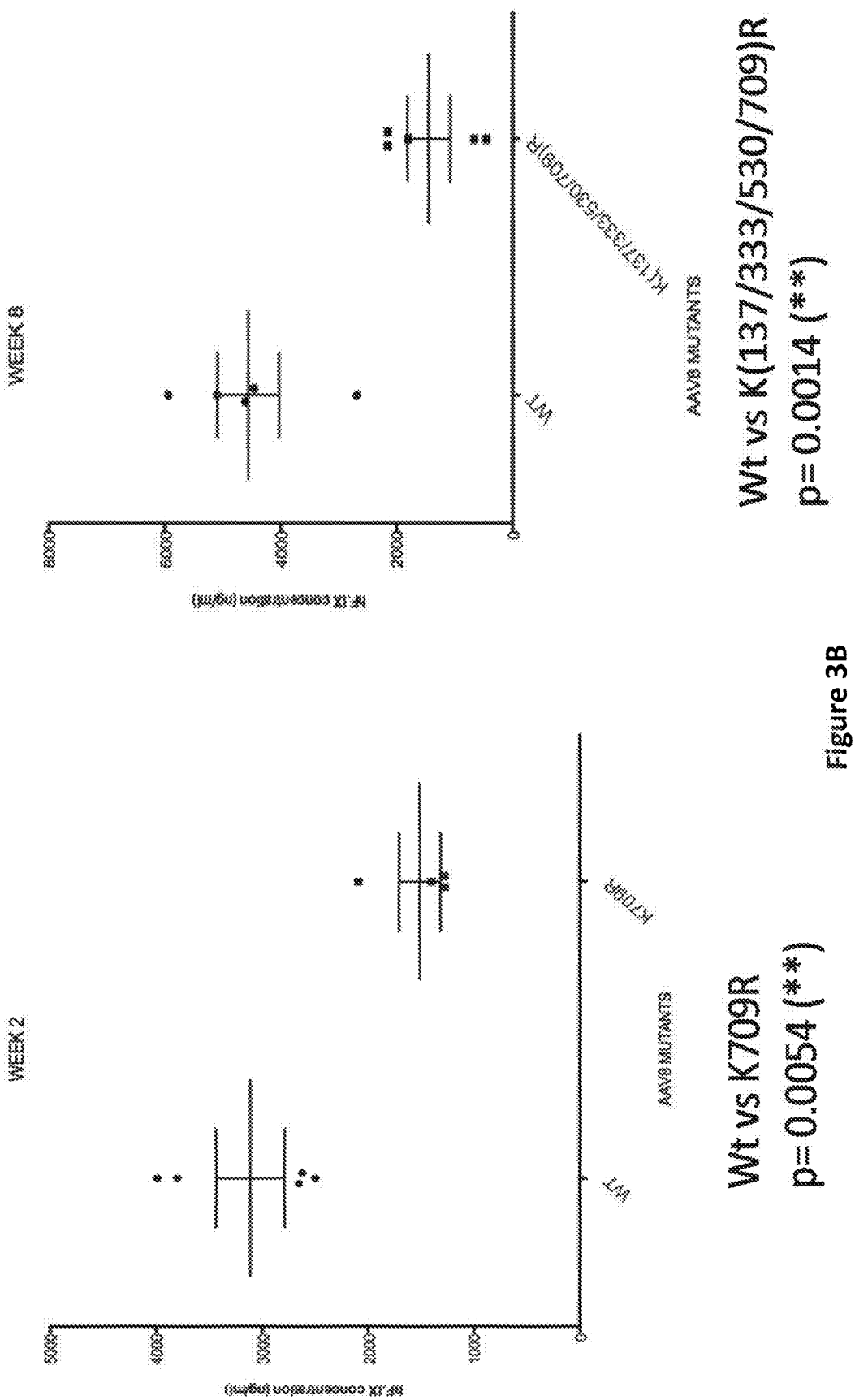
Figure 3C:
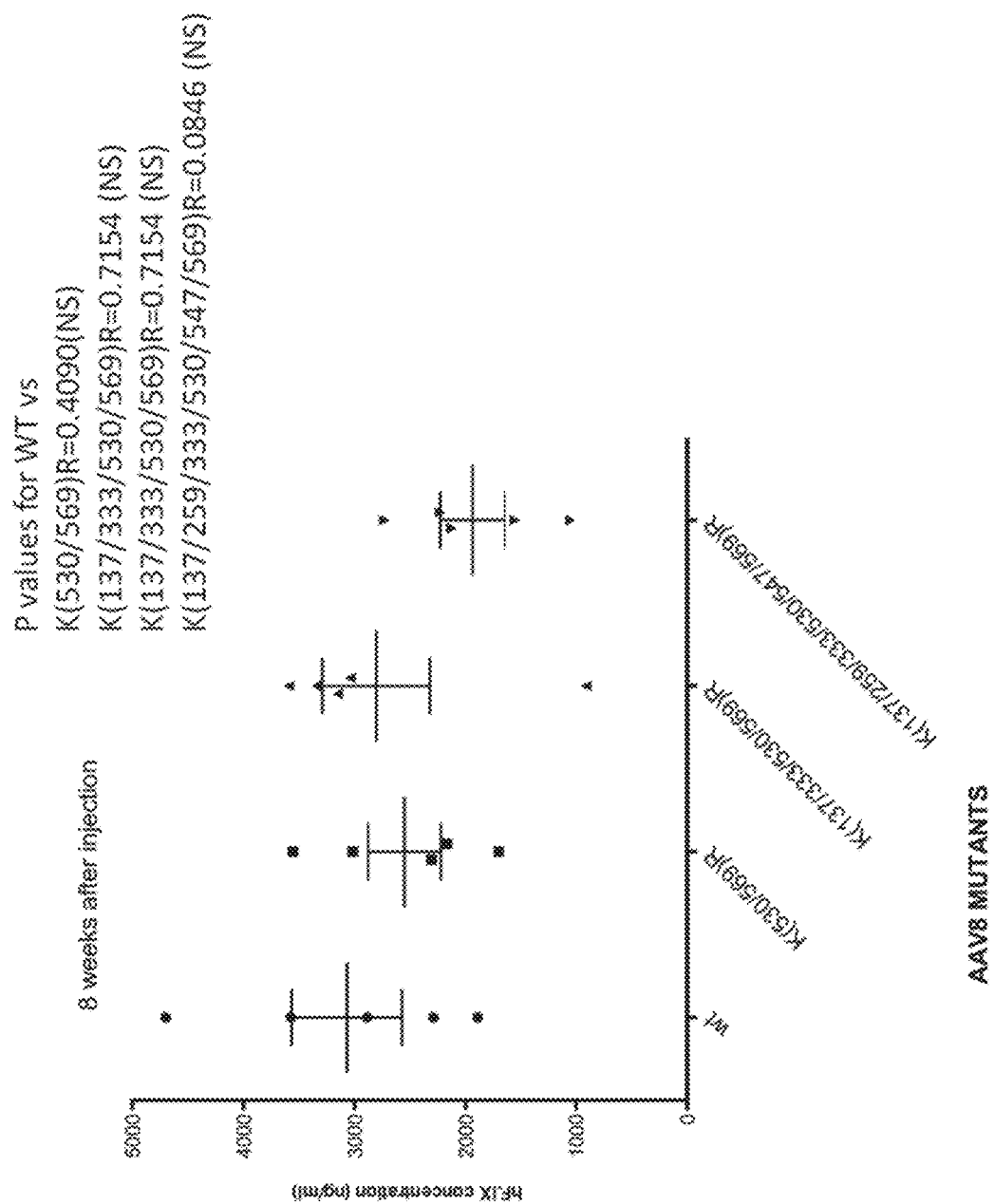
Figure 3D:
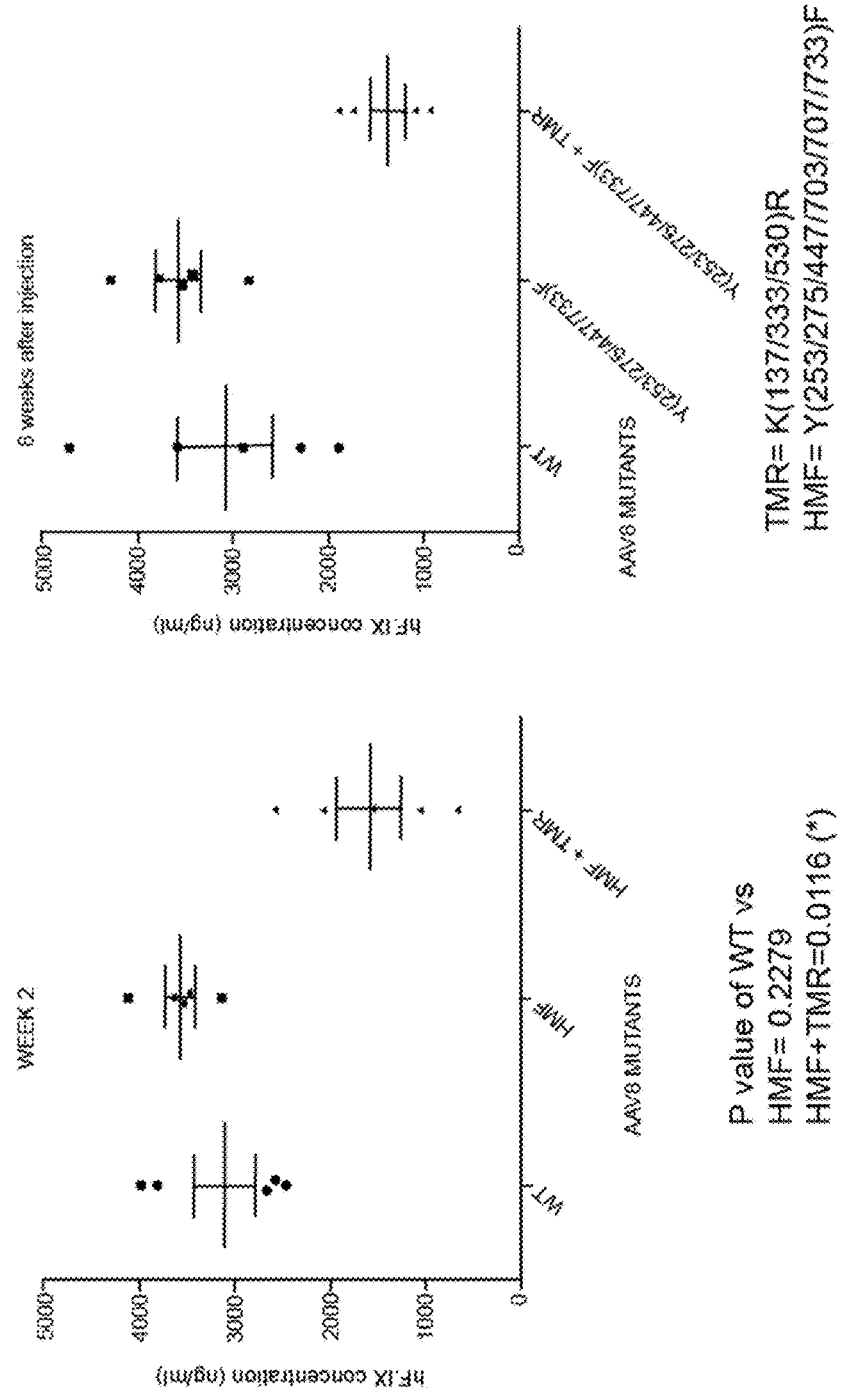

FIG. 1 shows schematic diagrams of the capsid surface. The data presented in FIGS. 2A, 2B and 2C demonstrate that altering lysine residues in the VP1 capsid on AAV8 alters the level of transgene produced due to altered transduction levels. FIGS. 3A, 3B and 3C show the effects of single and multiple mutations on HF.IX production in transduced cells. FIG. 3D demonstrates that a combination mutations, e.g., three lysine to arginine residues with four or six tyrosine to phenylalanine residues decreases transduction rates.

CTL Killing of HHL5-B7 Hepatocytes using AAV Lysine Mutants

We assessed CTL killing of hepatocytes transduced with certain of the AAV lysine mutants disclosed here. The following materials and methods were employed to assess CTL killing of transduced hepatocytes.

Vector Generation

AAV vectors were produced in HEK-293 cells using a triple transfection approach as previously described (Matsushita, 1998) and purified with cesium chloride gradient centrifugation methods (Ayuso, 2010). AAV epitope peptides were synthesized by Genemed Synthesis and resuspended at a concentration of 5 mg/ml in 100% DMSO.

In Vitro Expansion of T Cells

Human PBMCs (Cellular Technology LTD) were thawed, washed, counted, and resuspended at a concentration of $2 \times 10^6$ cells/ml in AIM-V lymphocyte media (Gibco) containing 3% human serum (Bioreclamation), 1% L-glutamine (Gibco), and 1% penicillin/streptomycin (Gibco). For each expansion condition, $1 \times 10^6$ (500 µl) cells were added per well in a 24 well plate (BD Falcon) in a volume of 500 An additional $1 \times 10^6$ (500 µl) of autologous irradiated splenocytes (3000 rad) were also added to each well as feeder cells, along with 2.5 µg/ml of human β-2-microglobulin (Lee Biosolutions), and 10 ng/ml of human recombinant IL-7 (R&D Systems). Cells were expanded in the presence of AAV peptide at a final concentration of 10 µg/ml at 37° C. in 5% $CO_2$. Human IL-2 (Roche) at a concentration of 10 ng/ml was added to the cell culture after the first 24 hours and replenished every 48 hours thereafter. Cells were divided into new wells as necessary and antigenic stimulation (antigen and feeder cells) was repeated every 7-10 days for up to 3 rounds of restimulation.

CTL Assay

CTL assay was performed as previously described (Pien, 2009). Briefly, lactate dehydrogenase (LDH) release following CTL-mediated target lysis was measured with the CytoTox 96 Non Radioactive Cytotoxicity Assay (Promega). Four thousand HHL5 hepatocyte target cells were plated in each well of a Microtest Primaria flat-bottom 96-well plate (BD Falcon) in DMEM containing no serum. Target cells were transduced at an MOI of 5000, 50,000, and 500,000 of AAV capsid and incubated for 18 hours at 37° C. 5% $CO_2$. Following treatment and incubation, plated target cells were washed once with media prior to the addition of epitope-specific cytotoxic T lymphocytes, expanded as described above. CTLs were added at an effector-target cell ratio of 10:1 for 4 hours at 37° C., 5% $CO_2$ and LDH was measured after a 30 minute incubation at room temperature with enzymatic substrate read at 490 nm using a spectrophotometer (Spectramax).

Flow Cytometry

GFP expression following AAV transduction was measured by flow cytometry. Human hepatocytes from cell lines HHL5 or Huh7 were plated in DMEM containing 10% fetal bovine serum, 1% L-glutamine (Gibco), and 1% penicillin/streptomycin (Gibco) at a density of 250,000 cells/well in a Primaria Multiwell 24-well plate (BD Falcon). Cells were transduced with 5000, 50000, or 5000000 MOI of AAV vector and incubated for 18 hours at 37° C. 5% $CO_2$. Following incubation, cells were trypsinized, washed twice with PBS 2% FBS, and fixed with 2% paraformaldehyde. Samples were aquired on a FACS Canto II flow cytometer using the FACSDiva® (BD Biosciences) and further analysis was performed using Flowjo® software (Treestar).

CTL Assay Results

Figure 4A:
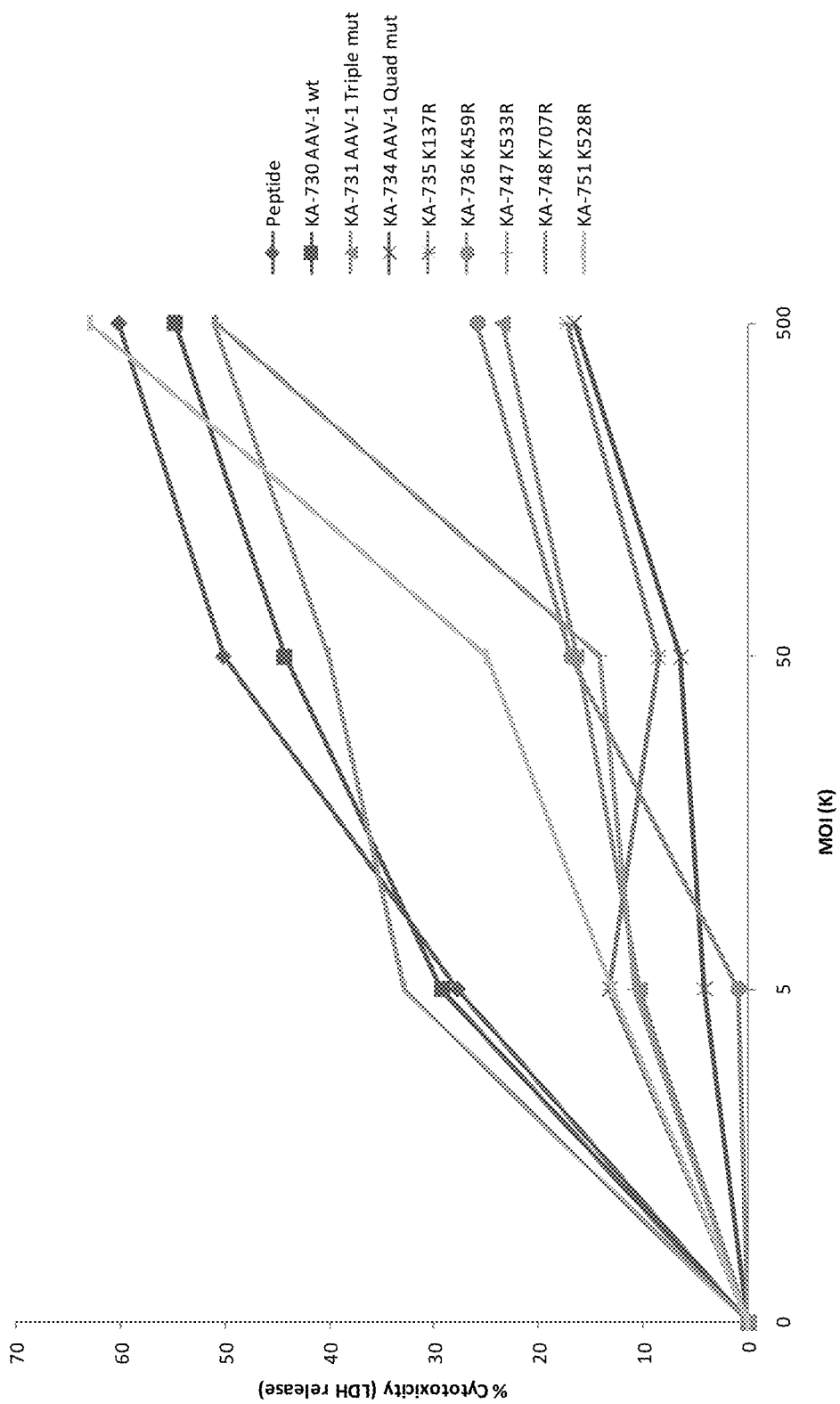
FIGS. 4A-4B: AAV1 transduction (FIG. 4A) CTL killing of HHL5-B7 hepatocytes transduced with AAV-1 lysine mutants at three different MOIs 5K, 50K and 500K. Peptide (IPQYGYLTL (SEQ ID NO:61) for AAV1; VPQYGYLTL (SEQ ID NO:62) for AAV2) was used as a positive control. LDH release correlates with the cell killing.
Figure 4B:
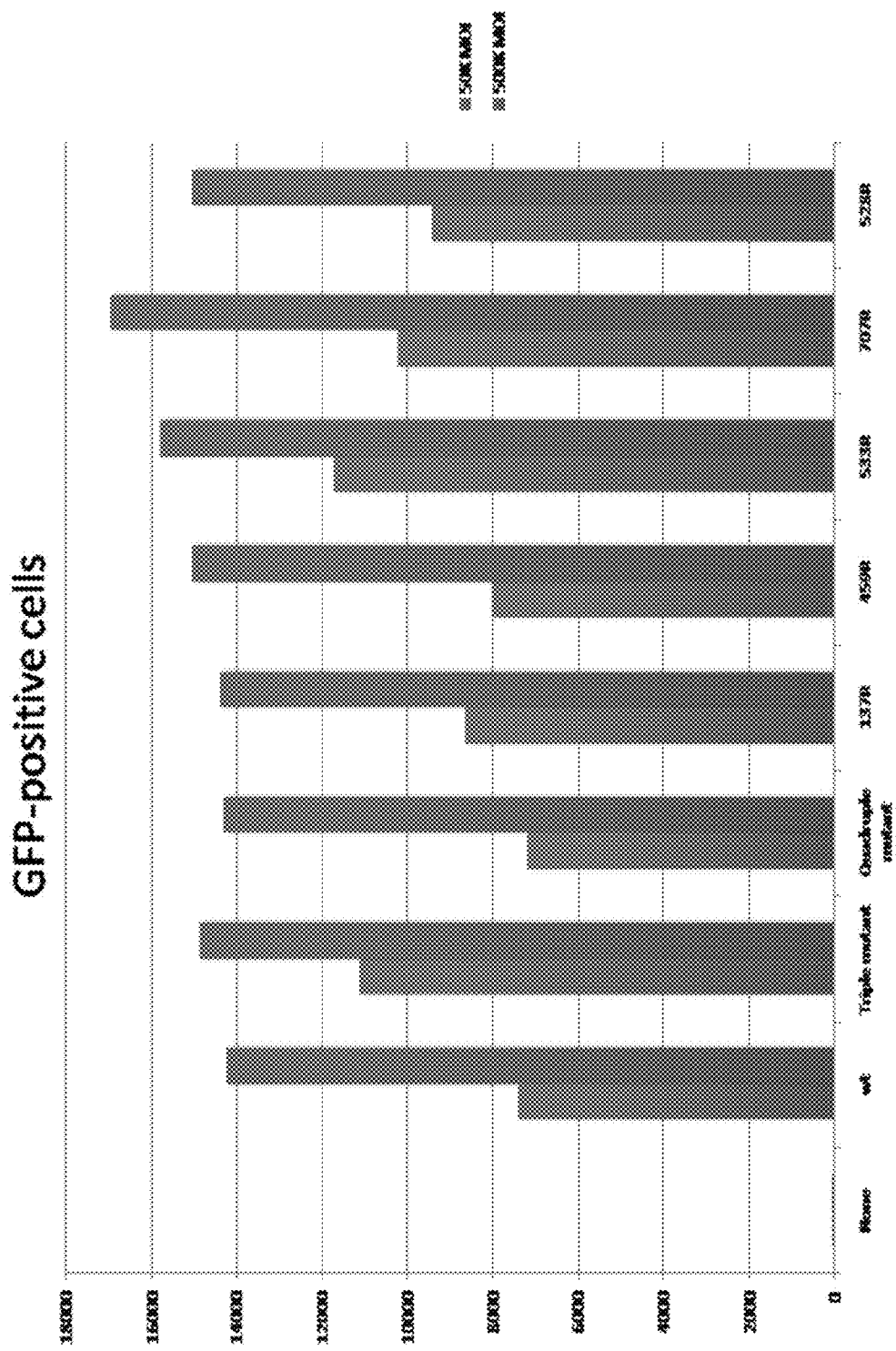
Figure 5A:
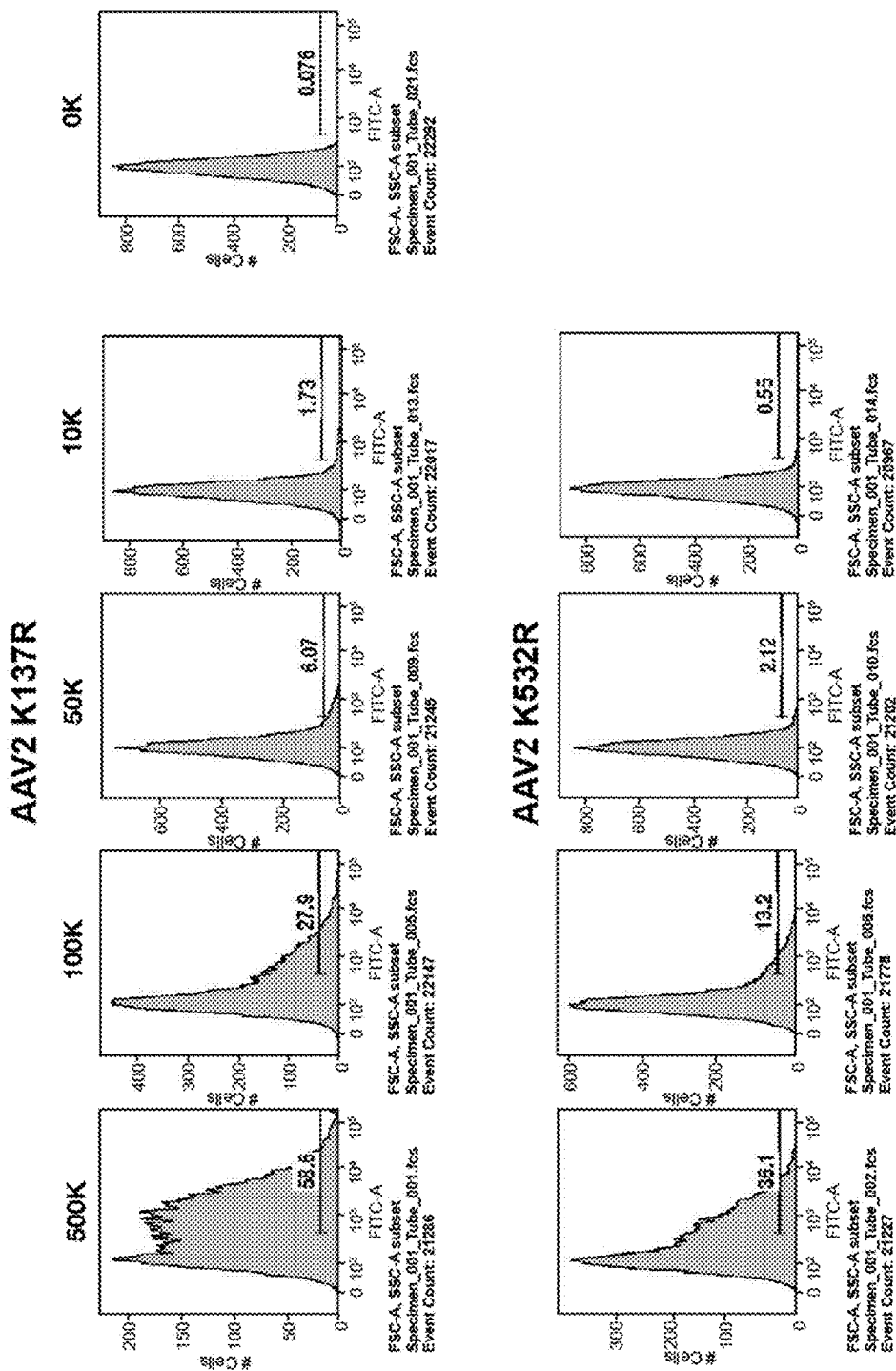
FIGS. 5A-5B: AAV2 transduction.
Figure 5A:
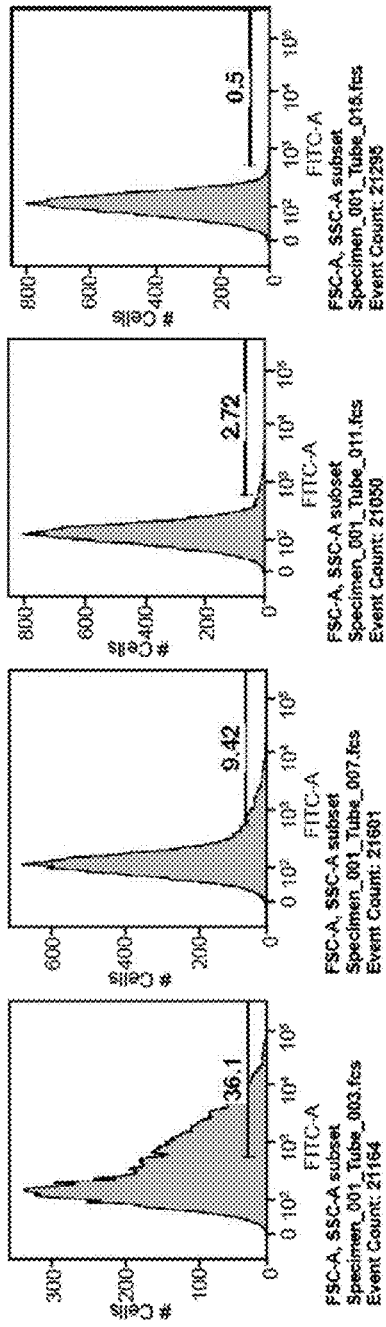
Figure 5A:
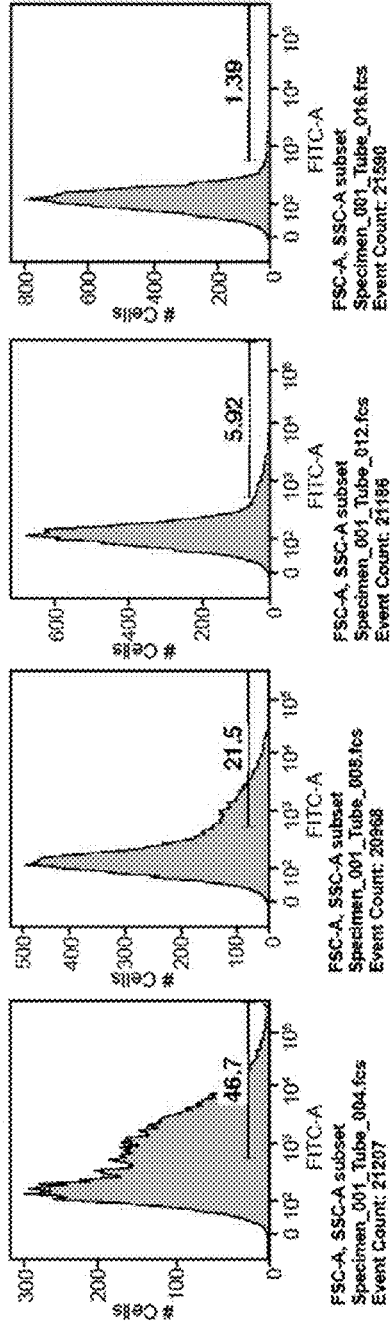
Figure 5B:
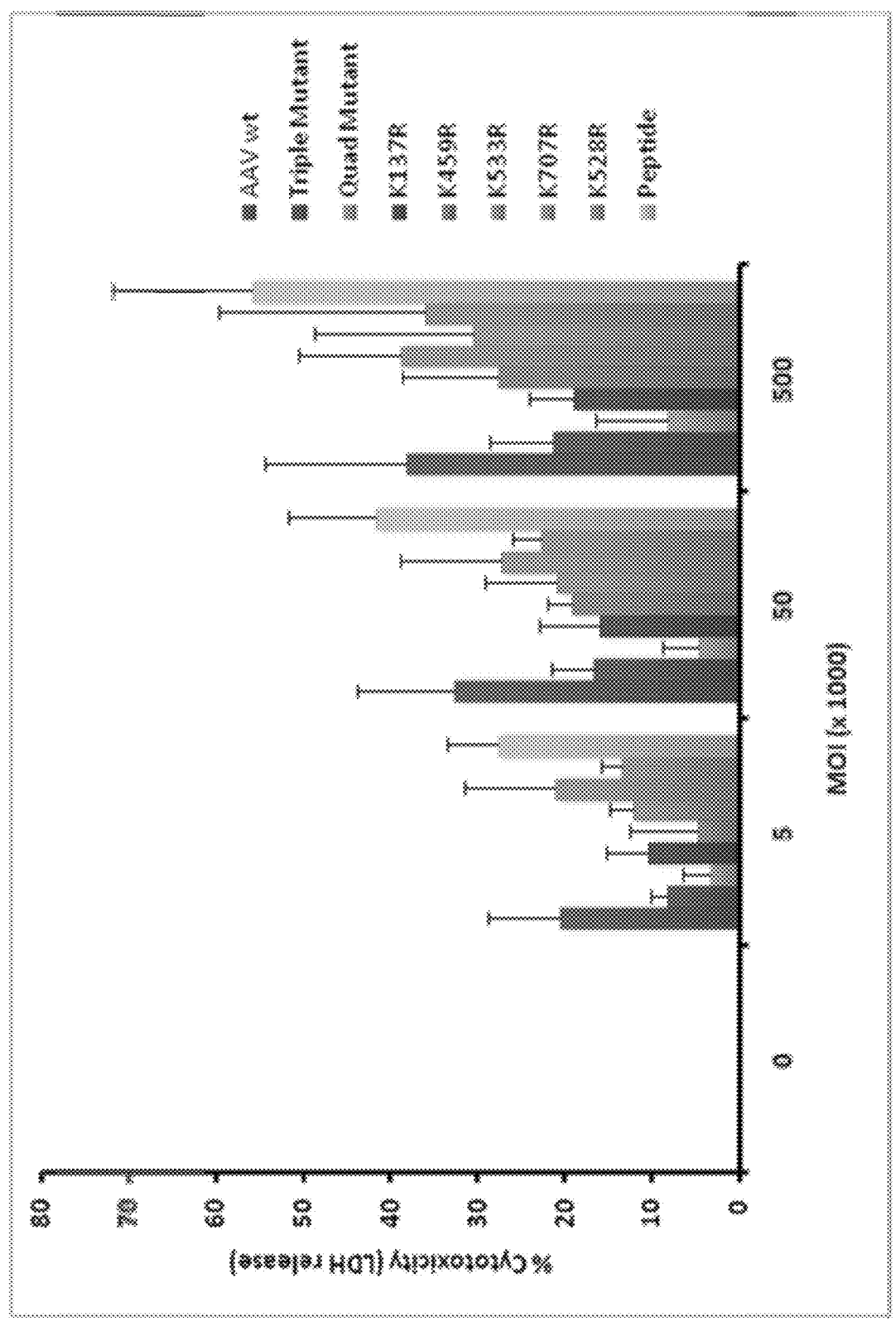
Figure 6:
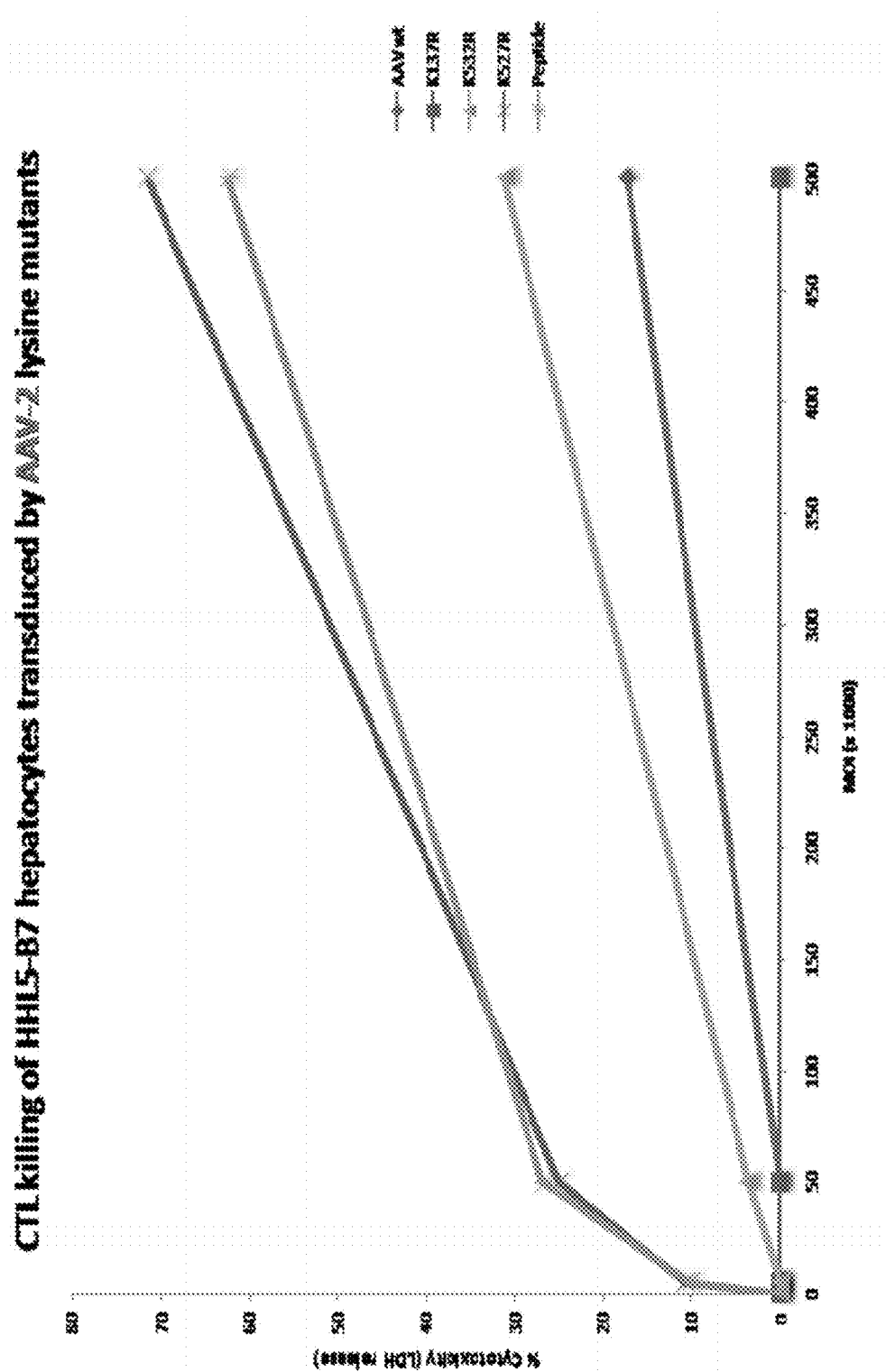
FIG. 6: CTL assay in which target hepatocyte cells were transduced with AAV-2 vector at increasing concentrations and then incubated with HLA-matched effector cells. AAV vectors encoded wild-type AAV-2 capsid or single lysine mutations as indicated. Effectors were derived from PBMC expanded in vitro against AAV-2 MHC Class I epitope VPQYGYLTL (SEQ ID NO:621 and effector-to-target ratio was 10:1. Results are expressed as percentage of CTL activity (% cytotoxicity compared to cells treated with 10% SDS as a maximum cytotoxicity control after background subtraction) with respect to the wild type vector.
Figure 7A:
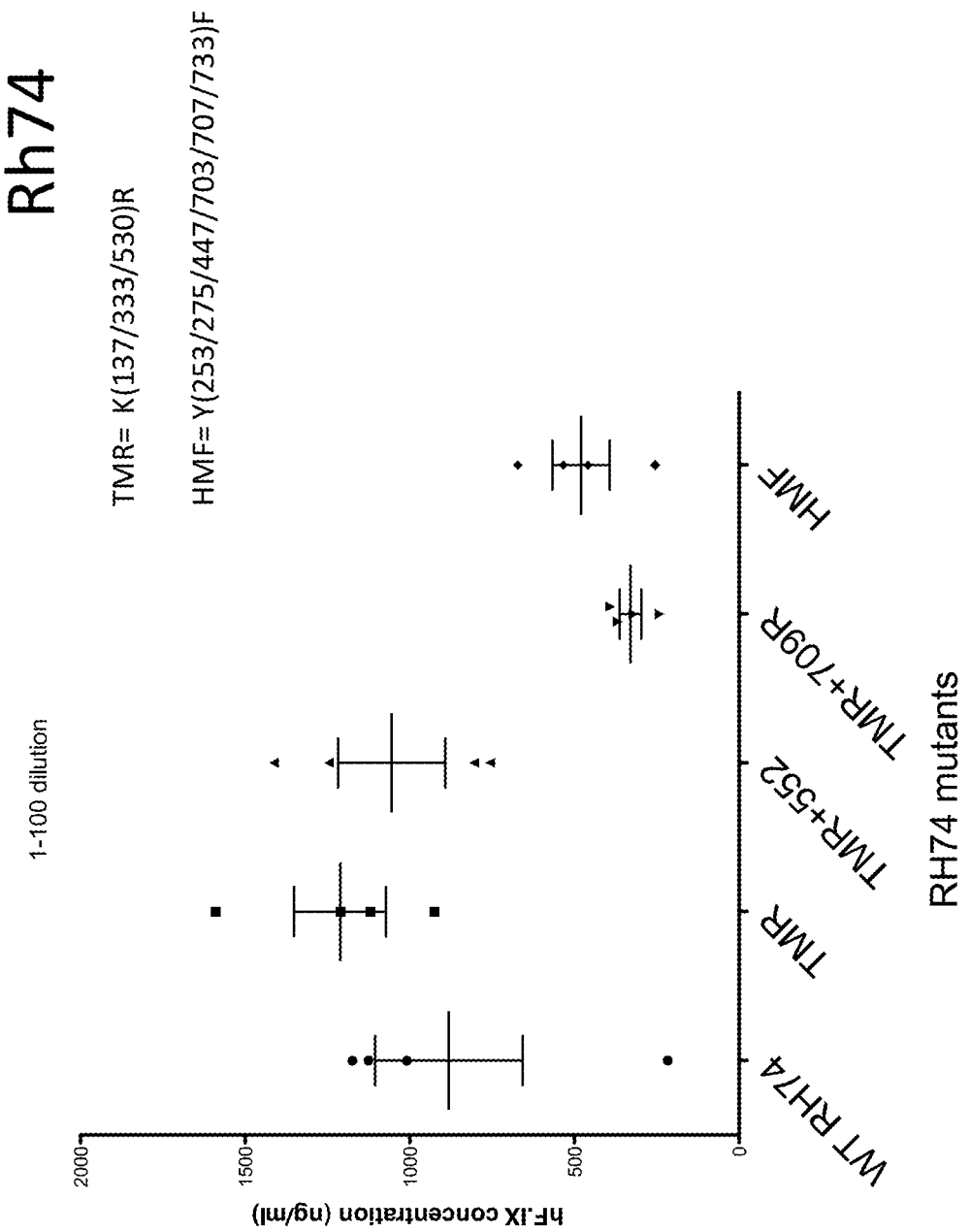
FIGS. 7A-7D: RH74 data: Human F.IX transgene expression levels in plasma measured by an ELISA specific for human F.IX.
Figure 7B:
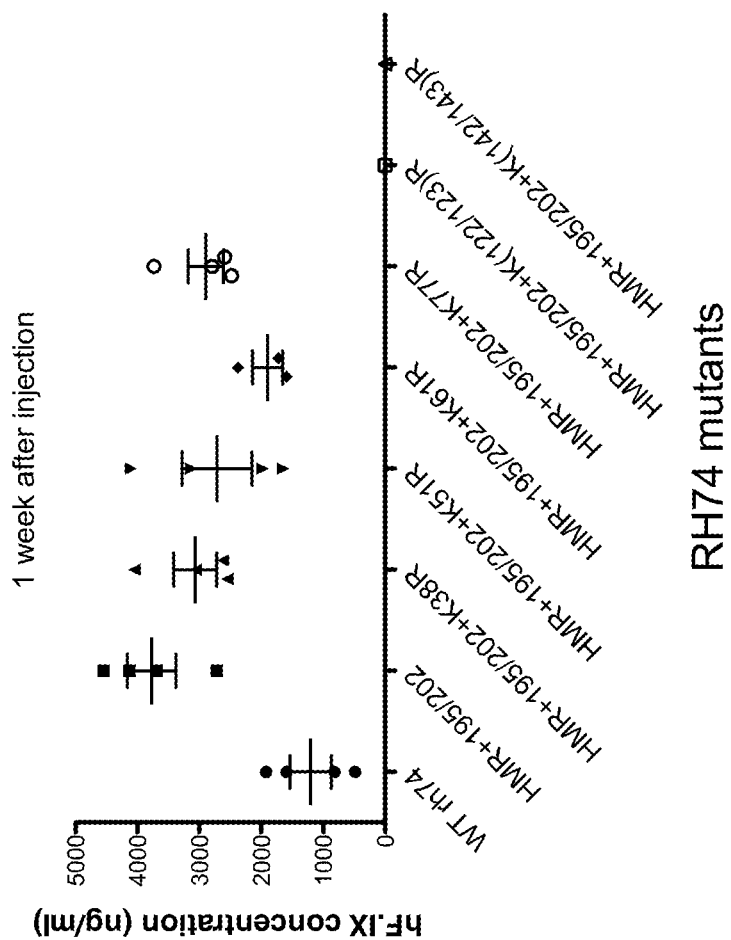
Figure 7C:
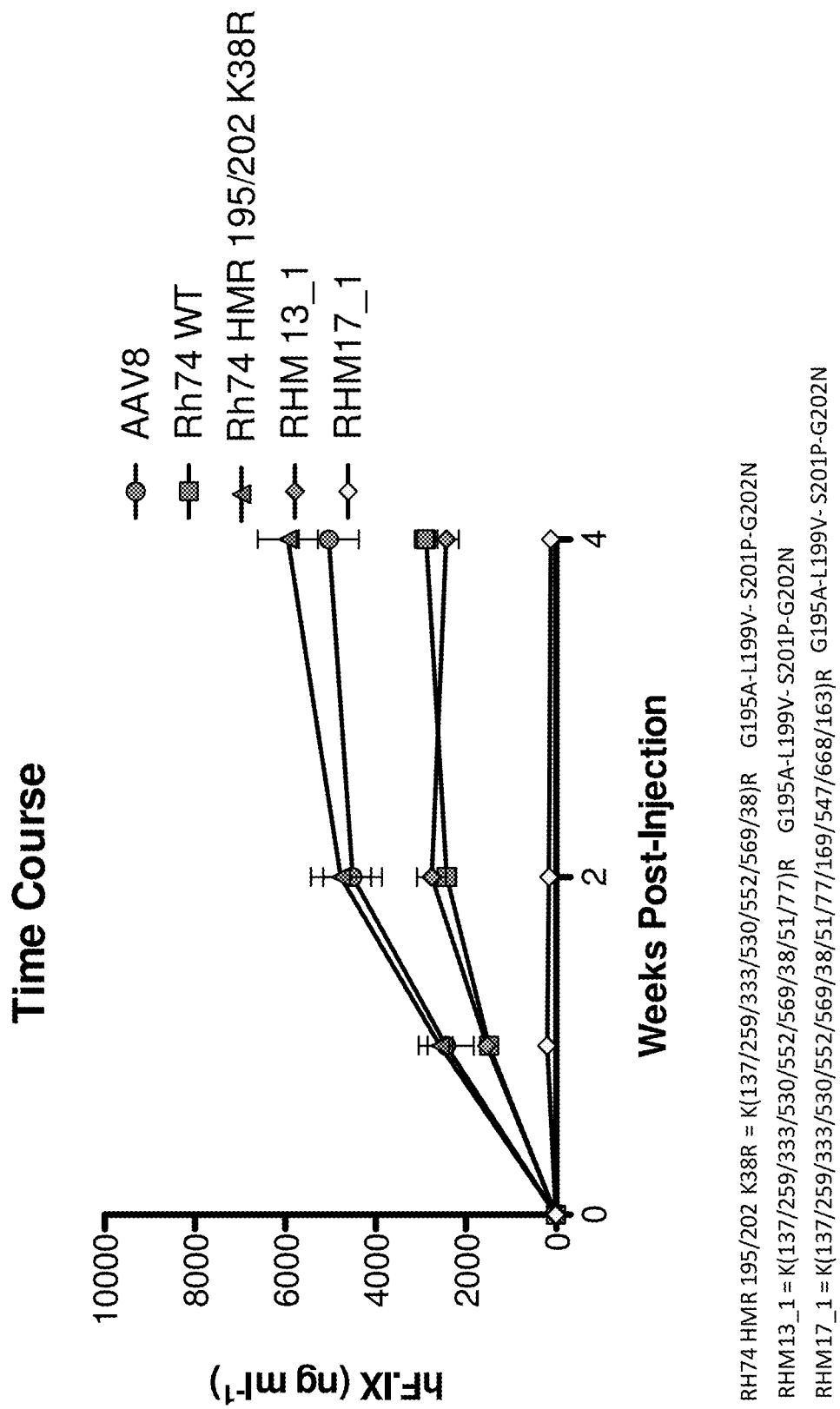
Figure 7D:
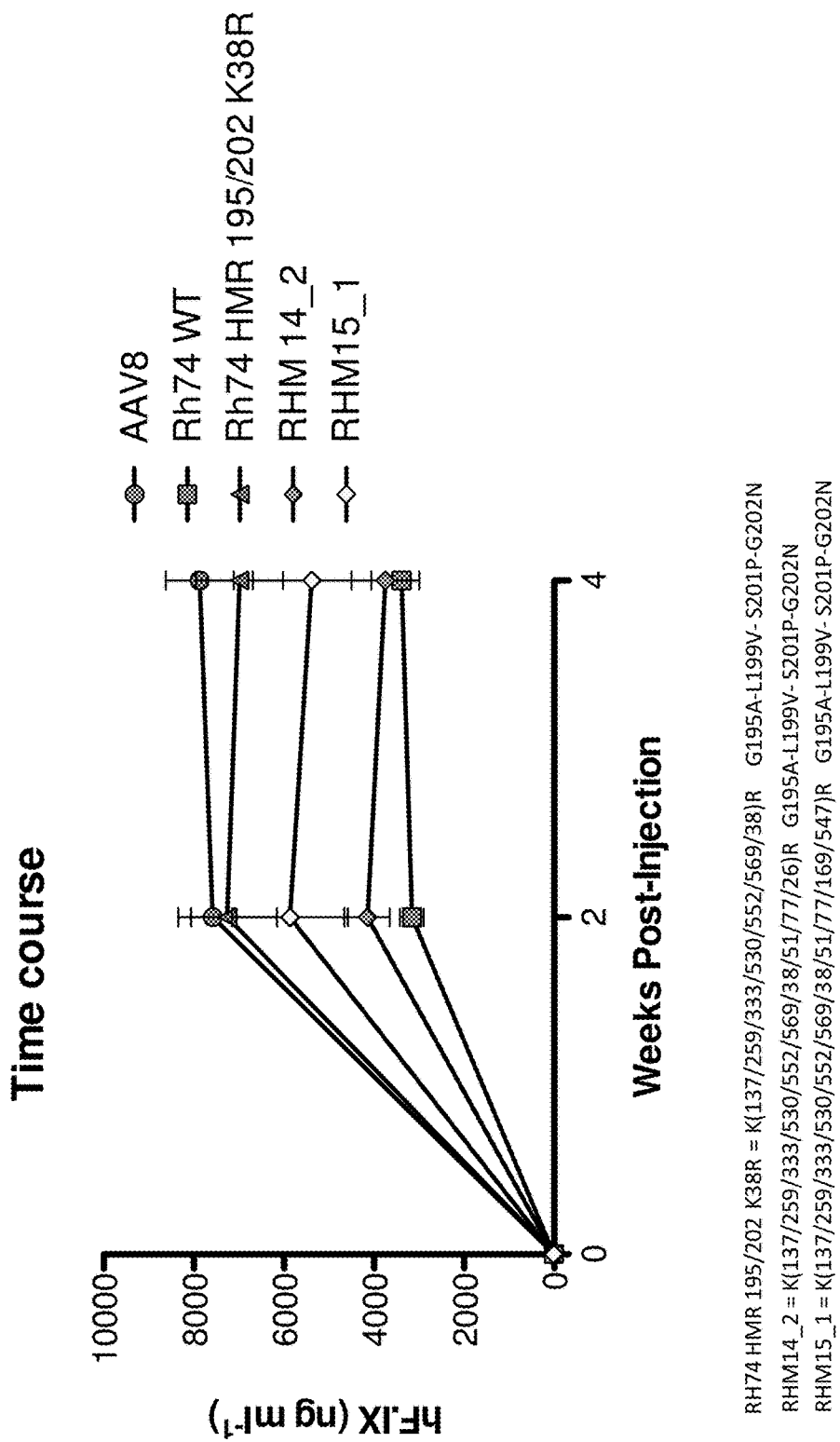

In order to further test effect of the lysine mutations on viral transduction, we utilized an in vitro CTL-mediated cytotoxicity assay previously developed by our lab to test the functionality of AAV vectors (Pien et al.). AAV1 and AAV2 transduction results are shown in FIGS. 4 and 5 and 6. In FIG. 4, all lysine mutations in the AAV-1 capsid resulted in a decrease in CTL-mediated killing of target cells, suggesting that the lysine mutations led to less efficient processing and presentation of surface antigen upon transduction. Furthermore, the effect of lysine mutations appears to be additive, with the triple and quadruple lysine mutants showing the greatest decrease of CTL-mediated killing (FIG. 4A, B). Mutations to the AAV-2 capsid showed a similar effect. See FIGS. 5 and 6. FIG. 7 shows the transduction results obtained when Rh74 variants were tested.

In summary, we have found that mutating the lysine residues on AAV capsids to arginine residues increases AAV transduction efficiency. Our experiments identified several variants that upon transduction, resulted in higher levels of expression of the human factor IX (FIX) transgene in mice compared to animals receiving unmodified AAV vectors.

REFERENCES

Xie Q, Bu W, Bhatia S, Hare J, Somasundaram T, Azzi A, et al. The atomic structure of adeno-associated virus (AAV-2), a vector for human gene therapy. *Proc Natl Acad Sci USA.* 2002; 99:10405-10410

High K A, Aubourg P "rAAV human trial experience" Methods Mol Biol. 2011; 807:429-57.

Zhong L, Zhao W, Wu J, Li B, Zolotukhin S, Govindasamy L, Agbandje-McKenna M, Srivastava A. "A dual role of EGFR protein tyrosine kinase signaling in ubiquitination of AAV2 capsids and viral second-strand DNA synthesis." Mol Ther. 2007 July; 15(7):1323-30. Epub 2007 Apr. 17.

Zhong L, Li B, Mah C S, Govindasamy L, Agbandje-McKenna M, Cooper M, Herzog R W, Zolotukhin I, Warrington K H Jr, Weigel-Van Aken K A, Hobbs J A, Zolotukhin S, Muzyczka N, Srivastava A. "Next generation of adeno-associated virus 2 vectors: point mutations in tyrosines lead to high-efficiency transduction at lower doses." Proc Natl Acad Sci USA. 2008 Jun. 3; 105(22):7827-32.

Thrower J S, Hoffman L, Rechsteiner M, and Pickart C M "Recognition of the polyubiquitin proteolytic signal." EMBO J. 2000 Jan. 4; 19(1): 94-102.

Bedford L, Lowe J, Dick L R, Mayer R J, Brownell J E. "Ubiquitin-like protein conjugation and the ubiquitin-proteasome system as drug targets" Nat Rev Drug Discov. 2011 January; 10(1):29-46

Peng, J; Schwartz; Elias; Thoreen; Cheng; Marsischky; Roelofs; Finley et al (August 2003). "A proteomics approach to understanding protein ubiquitination". *Nature biotechnology* 21 (8): 921-6.

Radivojac, P., Vacic, V., Haynes, C., Cocklin, R. R., Mohan, A., Heyen, J. W., Goebl, M. G., and Iakoucheva, L. M. Identification, Analysis and Prediction of Protein Ubiquitination Sites. *Proteins: Structure, Function, and Bioinfonnatics.* 78(2):365-380. (2010)

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of delivering a heterologous nucleic acid sequence to a cell in a subject, said method comprising the step of administering a pharmaceutical composition comprising an adeno-associated virus (AAV) vector comprising a VP1 capsid protein comprising one or more lysine substitutions at position 61, K61R, at position 84, K84R, at position 137, K137R, at position 143, K143R, at position 161, K161R, at position 459, K459R, at position 533, K533R, or at position 707, K707R of AAV1 VP1 capsid protein, said vector further comprising a minigene comprising AAV inverted terminal repeats and the heterologous nucleic acid sequence operably linked to regulatory sequences which direct expression of a product from the heterologous nucleic acid sequence in the cell.

2. A method of delivering a heterologous nucleic acid sequence to a cell in a subject, said method comprising the step of administering a pharmaceutical composition comprising an adeno-associated virus (AAV) vector comprising a VP1 capsid protein comprising one or more lysine substitutions at position 39, K39R, at position 137, K137R, at position 143, K143R, at position 161, K161R, at position 490, K490R, at position 527, K527R, or at position 532, K532R of AAV2 VP1 capsid protein, said vector further comprising a minigene comprising AAV inverted terminal repeats and the heterologous nucleic acid sequence operably linked to regulatory sequences which direct expression of a product from the heterologous nucleic acid sequence in the cell.

3. A method of delivering a heterologous nucleic acid sequence to a cell in a subject, said method comprising the step of administering a pharmaceutical composition comprising an adeno-associated virus (AAV) vector, comprising a VP1 capsid protein comprising one or more lysine substitutions at position 137, K137R, at position 259, K259R, at position 333, K333R, at position 530, K530R, at position 569, K569R, or at position 668, K668R, of AAV8 VP1 capsid protein, said vector further comprising a minigene comprising AAV inverted terminal repeats and the heterologous nucleic acid sequence operably linked to regulatory sequences which direct expression of a product from the heterologous nucleic acid sequence in the cell.

4. A method of delivering a heterologous nucleic acid sequence to a cell in a subject, said method comprising the step of administering a pharmaceutical composition comprising an adeno-associated virus (AAV) vector comprising a VP1 capsid protein comprising one or more lysine substitutions at position 26, K26R, at position 38, K38R, at position 51, K51R, at position 61, K61R, at position 77, K77R, at position 137, K137R, at position 169, K169R, at position 259, K259R, at position 333, K333R, at position 530, K530R, at position 547, K547R, at position 552, K552R, at position 569, K569R or at position 709, K709R of AAV-rh74 VP1 capsid protein, said vector further comprising a minigene comprising AAV inverted terminal repeats and the heterologous nucleic acid sequence operably linked to regulatory sequences which direct expression of a product from the heterologous nucleic acid sequence in the cell.

5. The method according to any one of claims 1-4, wherein the expression product of the heterologous nucleic acid sequence is a therapeutic peptide or nucleic acid.

6. The method according to claim 5, wherein the therapeutic peptide is a coagulation factor selected from the group consisting of Factor VIII, Factor IX or a functional fragment thereof.

7. The method according to any one of claims 1-4, wherein the expression product of the heterologous nucleic acid sequence is an IgG, IgM, IgA, IgD, IgE, chimeric immunoglobulin, humanized antibody, or a single chain antibody.

8. The method according to claim 7, wherein the expression product of the heterologous nucleic acid sequence is a chimeric immunoglobulin.

9. The method according to any one of claims 1-4, wherein the expression product of the heterologous nucleic acid sequence is a single chain antibody.

10. The method according to any one of claims 1-4, wherein the expression product is an antiviral RNAi or inhibitory RNA.

11. The method of claim 10, wherein said antiviral RNAi is effective to inhibit HCV infection and replication.

12. The method of claim 10, wherein said inhibitory RNA is effective to inhibit expression of a eukaryotic target gene.

13. The method according to any one of claims 1-4, wherein the expression product of the heterologous nucleic acid sequence is a disease-modifying cytokine.

14. The method according to any one of claims 1-4, wherein the expression product of the heterologous nucleic acid sequence is a pair of zinc finger nucleases.

15. The method according to any one of claims 1-4 comprising 2, 3, or 4 lysine substitutions.

16. The method according to any one of claims 1-4, wherein the expression product is Factor VIII.

17. The method according to any one of claims 1-4, wherein the expression product is Factor IX.

* * * * *

SEQUENCE LISTING

```
<160> NUMBER OF SEQ ID NOS: 62

<210> SEQ ID NO 1
<211> LENGTH: 735
<212> TYPE: PRT
<213> ORGANISM: Adeno-associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

```
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
```

-continued

```
Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro
                725                 730                 735

<210> SEQ ID NO 2
<211> LENGTH: 738
<212> TYPE: PRT
<213> ORGANISM: Adeno-associated virus 8

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175
```

```
Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
            530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590
```

-continued

```
Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 3
<211> LENGTH: 735
<212> TYPE: PRT
<213> ORGANISM: Adeno-associated virus 2

<400> SEQUENCE: 3

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

-continued

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
```

```
                    645                 650                 655
Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 4
<211> LENGTH: 738
<212> TYPE: PRT
<213> ORGANISM: Adeno-associated virus rh.74

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Ser Pro Val Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285
```

-continued

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu

```
                    705                 710                 715                 720
                Gly Thr Tyr Ser Glu Pro Arg Pro Ile Gly Thr Arg Tyr Leu Thr Arg
                                    725                 730                 735
                Asn Leu

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
cttcaacgga ctcgacaggg gggagcc                                             27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
ggctcccccc tgtcgagtcc gttgaag                                             27

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gcctacgacc agcagctcag agcgggtgac                                          30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gtcacccgct ctgagctgct ggtcgtaggc                                          30

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
tggttgagga aggcgctagg acggctcct                                           29

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
aggagccgtc ctagcgcctt cctcaacca                                           29
```

```
<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
ctaagacggc tcctggaaag agacgtccgg tag                                   33

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
ctaccggacg tctctttcca ggagccgtct tag                                   33

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
cgggcatcgg caggacaggc cagca                                            25

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
tgctggcctg tcctgccgat gcccg                                            25

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
agtccggaag tgcccaaaac agggacttgc tgt                                   33

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
acagcaagtc cctgttttgg gcacttccgg act                                   33

<210> SEQ ID NO 17
<211> LENGTH: 33
<212> TYPE: DNA
<213> ORGANISM: Artificial Sequence
<220> FEATURE:
<223> OTHER INFORMATION: primer
```

<400> SEQUENCE: 17
gcactgctat ggcctcacac agagacgacg aag                          33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
cttcgtcgtc tctgtgtgag gccatagcag tgc                          33

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19
caaagacgac gaagacaggt tctttcccat gagcg                        35

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20
cgctcatggg aaagaacctg tcttcgtcgt ctttg                        35

<210> SEQ ID NO 21
<211> LENGTH: 39
<212> TYPE: DNA
<213> ORGANISM: Artificial Sequence
<220> FEATURE:
<223> OTHER INFORMATION: primer

<400> SEQUENCE: 21
tgcagtacac atccaattat gcaagatctg ccaacgttg                    39

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
caacgttggc agatcttgca taattggatg tgtactgca                    39

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
ggttgaggaa ggcgctagga cggctcctgg                              30

<210> SEQ ID NO 24

```
<211> LENGTH: 30
<212> TYPE: DNA
<213> ORGANISM: Artificial Sequence
<220> FEATURE:
<223> OTHER INFORMATION: primer

<400> SEQUENCE: 24
ccaggagccg tcctagcgcc ttcctcaacc                                       30

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
gcagaatgaa ggcaccagga ccatcgccaa taacc                                 35

<210> SEQ ID NO 26
<211> LENGTH: 35
<212> TYPE: DNA
<213> ORGANISM: Artificial Sequence
<220> FEATURE:
<223> OTHER INFORMATION: primer

<400> SEQUENCE: 26
ggttattggc gatggtcctg gtgccttcat tctgc                                 35

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
gcatcgctat ggcaacacac agagacgacg agg                                   33

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
cctcgtcgtc tctgtgtgtt gccatagcga tgc                                   33

<210> SEQ ID NO 29
<211> LENGTH: 41
<212> TYPE: DNA
<213> ORGANISM: Artificial Sequence
<220> FEATURE:
<223> OTHER INFORMATION: primer

<400> SEQUENCE: 29
gtacacctcc aactactaca gatctacaag tgtggactttt g                         41

<210> SEQ ID NO 30
<211> LENGTH: 41
<212> TYPE: DNA
<213> ORGANISM: Artificial Sequence
<220> FEATURE:
<223> OTHER INFORMATION: primer

<400> SEQUENCE: 30
```
caaagtccac acttgtagat ctgtagtagt tggaggtgta c    41

<210> SEQ ID NO 31
<211> LENGTH: 27
<212> TYPE: DNA
<213> ORGANISM: Artificial Sequence
<220> FEATURE:
<223> OTHER INFORMATION: primer

<400> SEQUENCE: 31
gcccgcagag cggcataggg acgacag    27

<210> SEQ ID NO 32
<211> LENGTH: 27
<212> TYPE: DNA
<213> ORGANISM: Artificial Sequence
<220> FEATURE:
<223> OTHER INFORMATION: primer

<400> SEQUENCE: 32
ctgtcgtccc tatgccgctc tgcgggc    27

<210> SEQ ID NO 33
<211> LENGTH: 32
<212> TYPE: DNA
<213> ORGANISM: Artificial Sequence
<220> FEATURE:
<223> OTHER INFORMATION: primer

<400> SEQUENCE: 33
cctggttgag gaacctgtta ggacggctcc gg    32

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ccggagccgt cctaacaggt tcctcaacca gg    32

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
agacggctcc gggaaaaagg aggccggta    29

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
taccggcctc cttttcccg gagccgtct    29

<210> SEQ ID NO 37
<211> LENGTH: 24
<212> TYPE: DNA

```
<213> ORGANISM: Artificial Sequence
<220> FEATURE:
<223> OTHER INFORMATION: primer

<400> SEQUENCE: 37
cctcgggaac cggaagggcg ggcc                                              24

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
ggcccgccct tccggttccc gagg                                              24

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
ccgccagcag cgagtatcaa ggacatctgc gg                                     32

<210> SEQ ID NO 40
<211> LENGTH: 32
<212> TYPE: DNA
<213> ORGANISM: Artificial Sequence
<220> FEATURE:
<223> OTHER INFORMATION: primer

<400> SEQUENCE: 40
ccgcagatgt ccttgatact cgctgctggc gg                                     32

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
cggccatggc aagccacagg gacgatgaa                                         29

<210> SEQ ID NO 42
<211> LENGTH: 29
<212> TYPE: DNA
<213> ORGANISM: Artificial Sequence
<220> FEATURE:
<223> OTHER INFORMATION: primer

<400> SEQUENCE: 42
ttcatcgtcc ctgtggcttg ccatggccg                                         29

<210> SEQ ID NO 43
<211> LENGTH: 37
<212> TYPE: DNA
<213> ORGANISM: Artificial Sequence
<220> FEATURE:
<223> OTHER INFORMATION: primer

<400> SEQUENCE: 43
acaaggacga tgaagaaagg tttttcctc agagcgg                                 37
```

<210> SEQ ID NO 44
<211> LENGTH: 37
<212> TYPE: DNA
<213> ORGANISM: Artificial Sequence
<220> FEATURE:
<223> OTHER INFORMATION: primer

<400> SEQUENCE: 44
ccgctctgag gaaaaaacct ttcttcatcg tccttgt                37

<210> SEQ ID NO 45
<211> LENGTH: 31
<212> TYPE: DNA
<213> ORGANISM: Artificial Sequence
<220> FEATURE:
<223> OTHER INFORMATION: primer

<400> SEQUENCE: 45
ctggttgaat cgccggttag gacggctcct g              31

<210> SEQ ID NO 46
<211> LENGTH: 31
<212> TYPE: DNA
<213> ORGANISM: Artificial Sequence
<220> FEATURE:
<223> OTHER INFORMATION: primer

<400> SEQUENCE: 46
gaccaactta gcggccaatc ctgccgagga c              31

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47
gcagaatgaa ggcaccagga ccatcgccaa taacc                  35

<210> SEQ ID NO 48
<211> LENGTH: 35
<212> TYPE: DNA
<213> ORGANISM: Artificial Sequence
<220> FEATURE:
<223> OTHER INFORMATION: primer

<400> SEQUENCE: 48
ggttattggc gatggtcctg gtgccttcat tctgc                  35

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
gttgccatgg ctacccacag ggacgacgaa                   30

<210> SEQ ID NO 50
<211> LENGTH: 30
<212> TYPE: DNA
<213> ORGANISM: Artificial Sequence
<220> FEATURE:

<223> OTHER INFORMATION: primer

<400> SEQUENCE: 50
ttcgtcgtcc ctgtgggtag ccatggcaac                                    30

<210> SEQ ID NO 51
<211> LENGTH: 35
<212> TYPE: DNA
<213> ORGANISM: Artificial Sequence
<220> FEATURE:
<223> OTHER INFORMATION: primer

<400> SEQUENCE: 51
ggaaacaggg agctggaaga gacaacgtgg actat                              35

<210> SEQ ID NO 52
<211> LENGTH: 35
<212> TYPE: DNA
<213> ORGANISM: Artificial Sequence
<220> FEATURE:
<223> OTHER INFORMATION: primer

<400> SEQUENCE: 52
atagtccacg ttgtctcttc cagctccctg tttcc                              35

<210> SEQ ID NO 53
<211> LENGTH: 35
<212> TYPE: DNA
<213> ORGANISM: Artificial Sequence
<220> FEATURE:
<223> OTHER INFORMATION: primer

<400> SEQUENCE: 53
ctaaccagcg aggaagaaat aaggaccacc aaccc                              35

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
gggttggtgg tccttatttc ttcctcgctg gttag                              35

<210> SEQ ID NO 55
<211> LENGTH: 30
<212> TYPE: DNA
<213> ORGANISM: Artificial Sequence
<220> FEATURE:
<223> OTHER INFORMATION: primer

<400> SEQUENCE: 55
cgagtgggag ctgcagaggg agaacagcaa                                    30

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
ttgctgttct ccctctgcag ctcccactcg                                    30

```
<210> SEQ ID NO 57
<211> LENGTH: 32
<212> TYPE: DNA
<213> ORGANISM: Artificial Sequence
<220> FEATURE:
<223> OTHER INFORMATION: primer

<400> SEQUENCE: 57
gctgcagaag gagaacagca gacgctggaa cc                                    32

<210> SEQ ID NO 58
<211> LENGTH: 32
<212> TYPE: DNA
<213> ORGANISM: Artificial Sequence
<220> FEATURE:
<223> OTHER INFORMATION: primer

<400> SEQUENCE: 58
ggttccagcg tctgctgttc tccttctgca gc                                    32

<210> SEQ ID NO 59
<211> LENGTH: 43
<212> TYPE: DNA
<213> ORGANISM: Artificial Sequence
<220> FEATURE:
<223> OTHER INFORMATION: primer

<400> SEQUENCE: 59
agtacacttc caactactac agatctacaa atgtggactt tgc                        43

<210> SEQ ID NO 60
<211> LENGTH: 43
<212> TYPE: DNA
<213> ORGANISM: Artificial Sequence
<220> FEATURE:
<223> OTHER INFORMATION: primer

<400> SEQUENCE: 60
gcaaagtcca catttgtaga tctgtagtag ttggaagtgt act                        43

<210> SEQ ID NO 61
<211> LENGTH: 9
<212> TYPE: PRT
<213> ORGANISM: Adeno-associated virus 1

<400> SEQUENCE: 61

Ile Pro Gln Tyr Gly Tyr Leu Thr Leu
1               5

<210> SEQ ID NO 62
<211> LENGTH: 9
<212> TYPE: PRT
<213> ORGANISM: Adeno-associated virus 2

<400> SEQUENCE: 62

Val Pro Gln Tyr Gly Tyr Leu Thr Leu
1               5
```